(12) United States Patent
Fontana et al.

(10) Patent No.: US 9,359,333 B2
(45) Date of Patent: *Jun. 7, 2016

(54) EFFICIENT PROCESS FOR THE PREPARATION OF LAPATINIB AND SALTS THEREOF BY MEANS OF NEW INTERMEDIATES

(71) Applicant: F.I.S.—Fabbrica Italiana Sintetici S.p.A., Montecchio Maggiore-Vicenza (IT)

(72) Inventors: Francesco Fontana, Longone al Segrino (IT); Alfredo Paio, Legnago (IT)

(73) Assignee: F.I.S.—Fabbrica Italiana Sintetiei, Montecchio Maggiore (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/804,828

(22) Filed: Jul. 21, 2015

(65) Prior Publication Data

US 2015/0322050 A1    Nov. 12, 2015

Related U.S. Application Data

(60) Continuation of application No. 14/624,997, filed on Feb. 18, 2015, now Pat. No. 9,169,236, which is a division of application No. 14/016,238, filed on Sep. 3, 2013, now Pat. No. 9,024,023.

(30) Foreign Application Priority Data

Jan. 14, 2013  (IT) ............................... VI2013A0003
Mar. 28, 2013  (IT) ............................... VI2013A0086

(51) Int. Cl.
  *C07D 405/14*    (2006.01)
  *C07D 405/04*    (2006.01)
  *C07C 309/30*    (2006.01)

(52) U.S. Cl.
  CPC ............ *C07D 405/04* (2013.01); *C07C 309/30* (2013.01); *C07D 405/14* (2013.01)

(58) Field of Classification Search
  CPC .................................................... C07D 405/14
  See application file for complete search history.

(56) References Cited

U.S. PATENT DOCUMENTS

| 7,157,466 | B2 | 1/2007 | McClure et al. |
| 9,024,023 | B2 | 5/2015 | Fontana et al. |
| 9,169,236 | B2 | 10/2015 | Fontana et al. |
| 2008/0051422 | A1 | 2/2008 | Tung |
| 2013/0005971 | A1 | 1/2013 | Chen et al. |
| 2015/0065710 | A1 | 3/2015 | Fontana et al. |
| 2015/0225376 | A1 | 8/2015 | Fontana et al. |

FOREIGN PATENT DOCUMENTS

| EP | 2 468 745 A1 | 6/2012 |
| WO | WO 2011/116634 A1 | 9/2011 |
| WO | WO 2014/170910 A1 | 10/2014 |

OTHER PUBLICATIONS

Sigma-Aldrich, "Amine Protection," © Dec. 22, 2011, accessed at www.sigmaaldrich.com/chemistry/chemistry-products.printerview. html?TablePage=16255174, 3 pages.

Kim, S., "Protecting Groups for Organic Synthesis," School of Pharmacy, Seoul National University, © Sep. 7, 2012 and May 21, 2009, accessed at www.snupharm.ac.kr/shkim/erp/erpmenus/research_pds/uploadfiled/Lecture-Protecting_Groups_for_Organic_Synthesis.pdf, 36 pages.

Unknown Author, "The Chemistry of Halogens," chemed.chem. purdue.edu, published on-line Apr. 14, 2009, accessed at http://web.archive.org/web/20090414155348/http://chemed.chem.purdue.edu/genchem/topicreview/bp/ch10/group7.php, accessed on May 23, 2014, 7 pages.

*Primary Examiner* — Noble Jarrell
*Assistant Examiner* — John S Kenyon
(74) *Attorney, Agent, or Firm* — Sterne, Kessler, Goldstein & Fox P.L.L.C.

(57) ABSTRACT

The present invention refers to a new efficient process for the synthesis of the active pharmaceutical ingredient Lapatinib and salts thereof.

In particular, the present synthesis is carried out employing new intermediates in which the amine function is protected by a group cleavable in basic milieu that provides a higher overall yield of the synthesis process.

22 Claims, 2 Drawing Sheets

EFFICIENT PROCESS FOR THE PREPARATION OF LAPATINIB AND SALTS THEREOF BY MEANS OF NEW INTERMEDIATES

CROSS-REFERENCE TO RELATED APPLICATIONS

This patent application is a Continuation of U.S. patent application Ser. No. 14/624,997, filed on Feb. 18, 2015, which is a Division of U.S. patent application Ser. No. 14/016,238, filed on Sep. 3, 2013, which claims priority to and benefit of Italian Patent Applications No. VI2013A000003 filed on Jan. 14, 2013 and No. VI2013A00086 filed on Mar. 28, 2013, the contents of which are incorporated herein by reference.

TECHNICAL FIELD

An object of the present invention is a new process for synthesis of the active pharmaceutical ingredient Lapatinib and salts thereof.

BACKGROUND ART

Lapatinib is an active pharmaceutical ingredient used for the treatment of advanced metastatic lung cancer and is currently on the market under the name Tykerb, sold by Glaxo-SmithKline (GSK).

According to the manufacturer's instructions, the commercial product Tykerb contains Lapatinib as the ditosylate monohydrate salt of formula (I-bis):

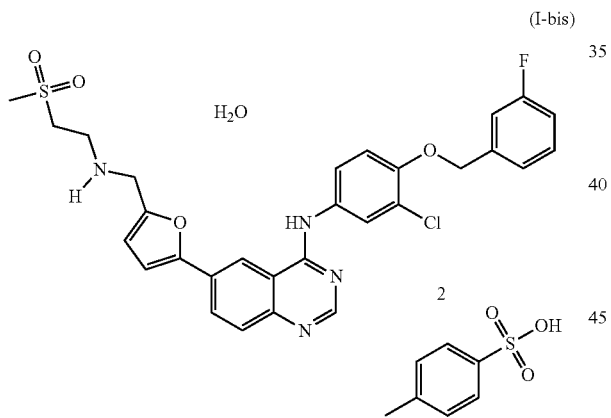

(I-bis)

having the chemical name N-{3-Chloro-4-[(3-fluorobenzyl)oxy]phenyl}-6-[5-({[2-(methylsulphonyl)ethyl]amino}methyl)furan-2-yl]quinazolin-4-amine bis(4-methylbenzenesulphonate) monohydrate, CAS RN 388082-78-8 and m.p. 250-256° C.

This substance can be prepared according to teachings of the prior art such as for example those contained in U.S. Pat. No. 7,157,466. In particular, in said reference, examples 10 and 11 show the preparation of the ditosylate monohydrate salt starting from the anhydrous ditosylate salt.

The aforementioned process suffers from the main disadvantage consisting in that said intermediates such as for example that having the aldehyde function in free form being poorly soluble, thus leading to low productivity. In other processes of the known art, stannane intermediates are used resulting in problems related to waste disposal. In general the known processes for the preparation of Lapatinb suffer of a low overall molar yield.

SUMMARY OF INVENTION

The problem addressed by the present invention regards the provision of an improved process for the preparation of Lapatinib and salts thereof, which allows at least partially overcoming the aforementioned drawbacks with reference to the prior art.

This problem is resolved through a process for the synthesis of Lapatinib as outlined in the attached claims, whose definitions are an integral part of the present description.

Further characteristics and advantages of the process according to the invention will be apparent from the description—indicated hereinafter—of preferred embodiments, provided by means of non-limiting example.

DESCRIPTION OF EMBODIMENTS

Figure 1:
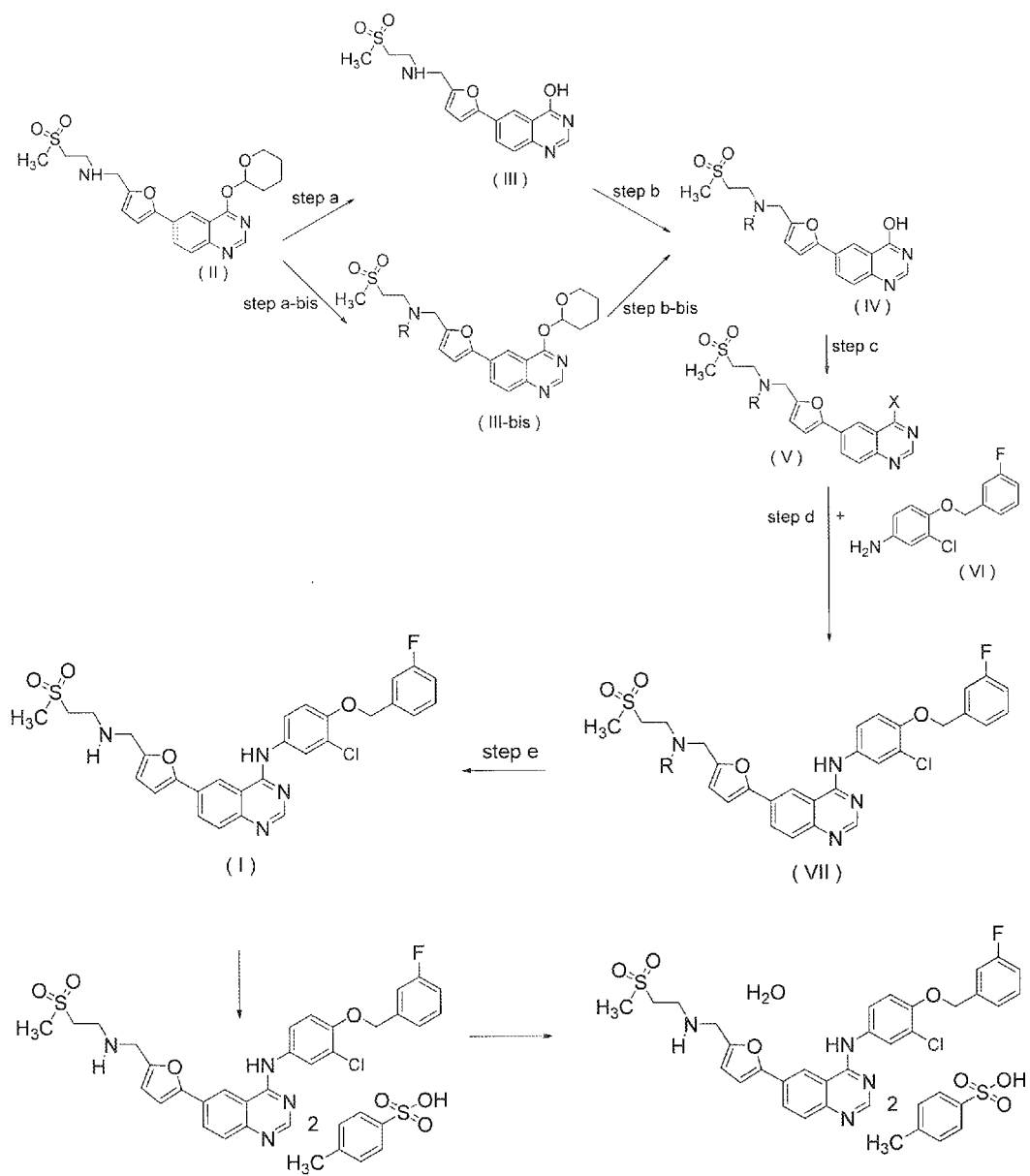
FIG. 1 shows the scheme of the process for the synthesis of Lapatinib according to the present invention.

The present invention concerns a process for the preparation of Lapatinib of formula (I) or a salt thereof:

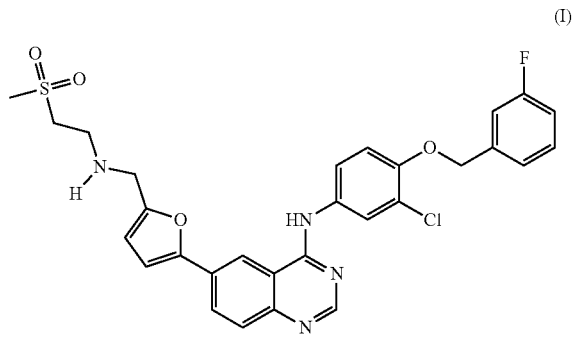 [SMILES: CS(=O)(=O)CCNCc1ccc(-c2ccc3ncnc(Nc4ccc(OCc5cccc(F)c5)c(Cl)c4)c3c2)o1]

(I)

comprising the following steps:
(a) Deprotection reaction of the compound 2-(methylsulphonyl)-N-({5-[4-(tetrahydro-2H-pyran-2-yloxy)quinazolin-6-yl]furan-2-yl}methyl) ethanamine of formula (II):

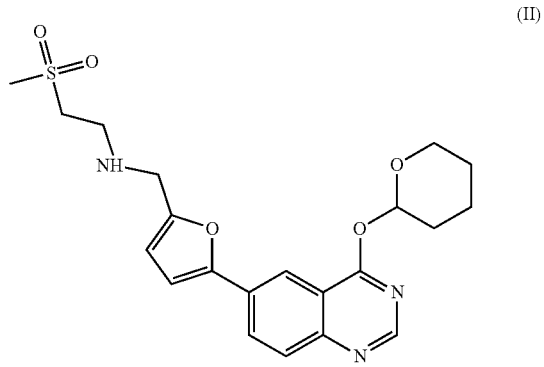 [SMILES: CS(=O)(=O)CCNCc1ccc(-c2ccc3ncnc(OC4CCCCO4)c3c2)o1]

(II)

to give the compound 6-[5-({[2-(methylsulphonyl)ethyl]amino}methyl)furan-2-yl]quinazolin-4-ole of formula (III) or a salt thereof:

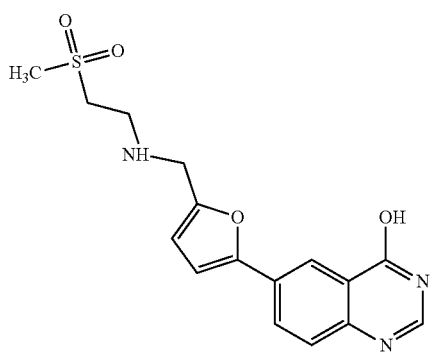

(III)

(b) Amine protection reaction of the intermediate of formula (III) to give the N-protected-6-[5-({[2-(methylsulphonyl)ethyl]amino}methyl) furan-2-yl]quinazolin-4-ole of formula (IV):

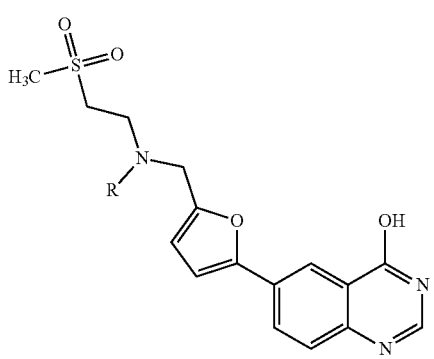

(IV)

wherein R is selected from the group of methyl oxycarbonyl, ethyl oxycarbonyl, 9-(2-Sulpho)fluorenylmethyl oxycarbonyl, 9-(2,7-Dibromo)fluorenylmethyl oxycarbonyl, 17-Tetrabenzo[a,c,g,i]fluorenylmethyl oxycarbonyl (Tbfmoc), 2-Chloro-3-indenylmethyl oxycarbonyl (Climoc), Benz[f]inden-3-ylmethyl oxycarbonyl (Bimoc), 2-Phosphonioethyl oxycarbonyl (Peoc), 1-Methyl-1-(triphenylphosphonium)ethyl (2-Triphenylphosphoniumisopropyl) oxycarbonyl (Ppoc), 1,1-Dimethyl-2-cyanoethyl oxycarbonyl, 2-Dansylethyl oxycarbonyl (Dnseoc), 2-(4-Nitrophenyl)ethyl oxycarbonyl (Npeoc), m-Chloro-p-acyloxybenzyl oxycarbonyl, 9-Fluorenylmethyl oxycarbonyl (Fmoc), formyl (CO)H, acetyl CH$_3$(CO), trifluoroacetyl CF$_3$(CO), difluoroacetyl CHF$_2$(CO), monofluoroacetyl CH$_2$F(CO), trichloracetyl CCl$_3$(CO), dichloroacetyl CHCl$_2$(CO), monochloroacetyl CH$_2$Cl(CO), 2-(Trimethylsilyl) ethanesulphonyl;

(c) Conversion of the intermediate of formula (IV) to give the N-protected-N-{[-(4-substituted-quinazolin-6-yl) furan-2-yl]methyl}-2-(methylsulphonyl)ethanamine of formula (V):

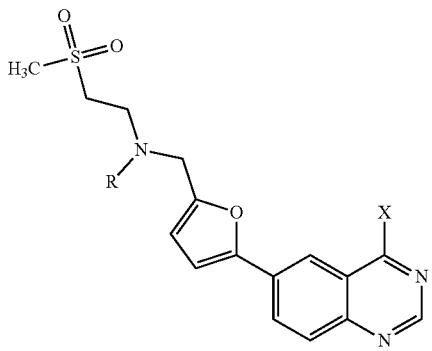

(V)

wherein R has the same meaning as described in step (b) and X is chosen in the group consisting of Fluorine, Chlorine, Bromine, Iodine, O-Ms (mesylate), O-Ts (tosylate), O-Tf (triflate), ethanesulfonate (esylate), benzenesulfonate (besylate), p-bromobenzenesulfonate (brosylate), p-nitrobenzenesulfonate (nosylate);

(d) Reaction of the intermediate of formula (V) with 3-chloro-4-[(3-fluorobenzyl)oxy]aniline of formula (VI):

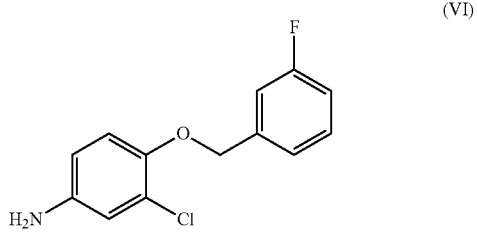

(VI)

to give the N-protected Lapatinib of formula (VII):

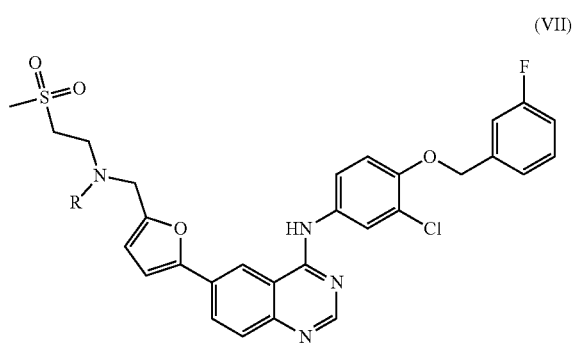

(VII)

wherein R has the same meaning as described in step (b);

(e) Deprotection reaction of N-protected Lapatinib of formula (VII) to give Lapatinib of formula (I) or salts thereof;

or, according an alternative embodiment of the process of the present invention, process wherein steps (a) and (b) are respectively substituted by the following steps:

(a-bis) Amine protection reaction of the intermediate of formula (II) to give the N-protected-2-(methylsulphonyl)-N-({5-[4-(tetrahydro-2H-pyran-2-yloxy)quinazolin-6-yl]furan-2-yl}methyl)ethanamine of formula (III-bis):

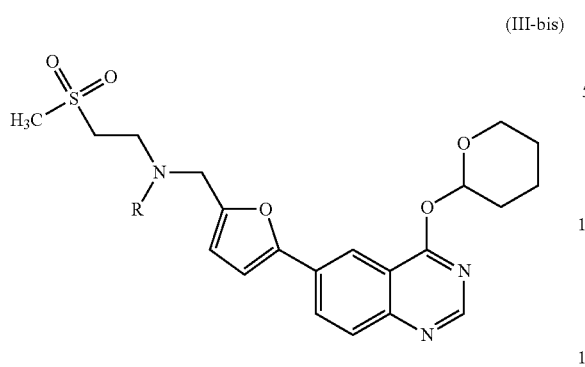

(III-bis)

wherein R has the same meaning as described in step (b);

(b-bis) Deprotection reaction of the intermediate of formula (III-bis) to give the N-protected-6-[5-({[2-(methylsulphonyl)ethyl]amino}methyl)furan-2-yl]quinazolin-4-ole of formula (IV):

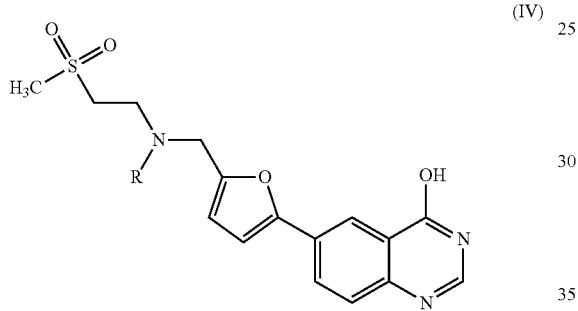

(IV)

wherein R has the same meaning as described in step (b).

The process of the present invention thus provides two alternative routes for the preparation of the key intermediate, according to the process of the present invention, for the synthesis of Lapatinib and salts thereof, namely the N-protected-6-[5-({[2-(methylsulphonyl)ethyl]amino}methyl)furan-2-yl]quinazolin-4-ole of formula (IV):

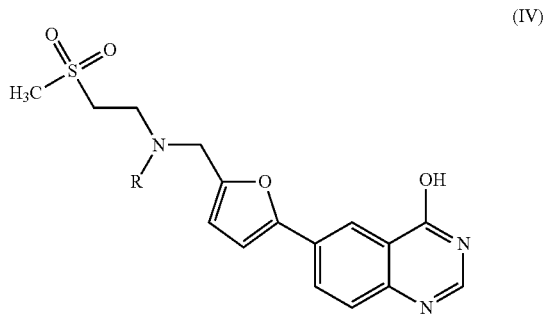

(IV)

wherein FR has the same meaning as described in step (b);

In particular, said process comprises the following steps:

(a) Deprotection reaction of the compound 2-(methylsulphonyl)-N-({5-[4-(tetrahydro-2H-pyran-2-yloxy)quinazolin-6-yl]furan-2-yl}methyl)ethanamine of formula (II):

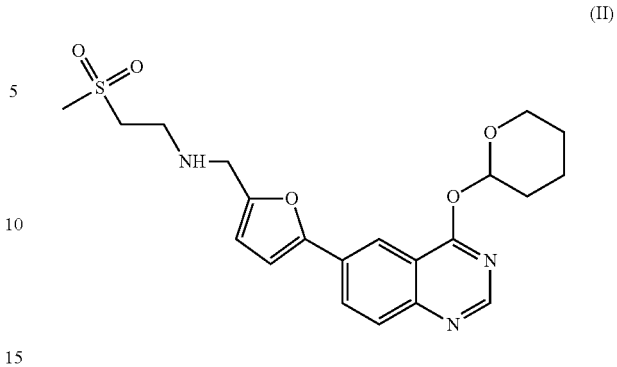

(II)

to give the compound 6-[5-({[2-(methylsulphonyl)ethyl]amino}methyl) furan-2-yl]quinazolin-4-ole of formula (III) or a salt thereof:

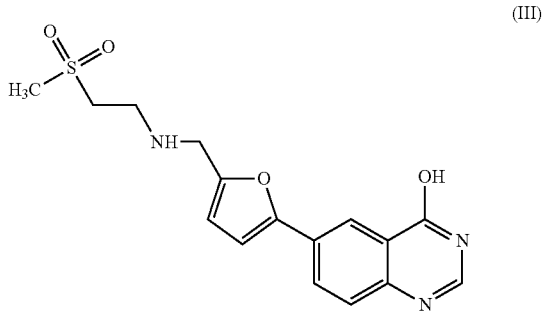 [SMILES: CS(=O)(=O)CCNCc1ccc(-c2ccc3ncnc(O)c3c2)o1]

(III)

(b) Amine protection reaction of the intermediate of formula (III) to give the compound of formula (IV);

Or, Alternatively, Comprising the Following Steps:

(a-bis) Amine protection reaction of the intermediate of formula (II) to give the N-protected-2-(methylsulphonyl)-N-({5-[4-(tetrahydro-2H-pyran-2-yloxy)quinazolin-6-yl]furan-2-yl}methyl)ethanamine of formula (III-bis):

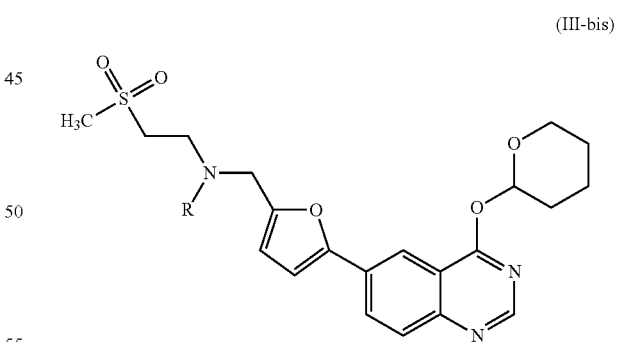

(III-bis)

wherein R has the same meaning as described in step (b) of claim 1;

(b-bis) Deprotection reaction of the intermediate of formula (III-bis) to give the compound of formula (IV).

All the amine function protecting groups that are cleavable under basic conditions can be employed to implement the present invention, according to the compounds of formula (IV), (V), (VII) and (III-bis), the compounds of which, since they cannot be specifically claimed, must be intended as comprised within the scope of protection of the present invention since they allow the application of said inventive concept.

Vice-versa, the intermediates of formula (IV), (V), (VII) and (III-bis) wherein R is Boc (t-BuO(CO)) are not comprised in the present invention since it is an amine function protection group that is not cleavable in basic conditions. The same applies to the compounds of formula (IV), (V), (VII) and (III-bis) wherein R is Z, i.e. Cbz, carbobenzyloxy.

For a more comprehensive description of the amine function protecting groups that are cleavable in basic conditions, please refer to the knowledge of those skilled in the field, which can be deduced from the work by T. W. Green, P. G. M. Wuts, Protective Groups in Organic Synthesis, Fourth Edition, Wiley-Interscience, New York, 2007 the content of which, with regard to the description of the aforementioned protecting groups, should be understood as comprised in the present invention.

In one preferred embodiment, the process of the present invention for the preparation of Lapatinib and its key intermediate of formula (IV) is conveniently carried out employing the intermediates of formula (IV), (V), (VII) and (III-bis) wherein R is trifluoroacetyl or Fmoc, i.e. 9-Fluorenylmethyl oxycarbonyl having the following structure:

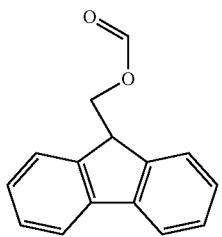 [SMILES: O=COCC1c2ccccc2-c2ccccc21]

In a more preferred embodiment of the process of the present invention for the preparation of Lapatinib and of its key intermediate of formula (IV), it is conveniently carried out using those intermediate compounds in which R is trifluoroacetyl since said group has a low molecular weight, allowing the handling of lower mass amounts of product and better atom-economy.

The compound of formula (IV) particularly preferred is therefore the 2,2,2-trifluoro-N-{[5-(4-hydroxyquinazolin-6-yl)furan-2-yl]methyl}-N-[2-(methylsulphonyl)ethyl]acetamide of formula (IV, R=CF$_3$(CO)):

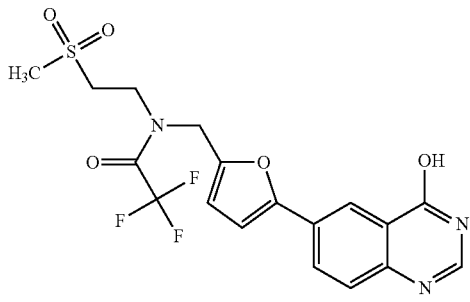

(IV, R = CF$_3$(CO))

Obviously, the compound of formula (IV) can also be in the following tautomeric form, which is therefore comprised in the scope of the present invention.

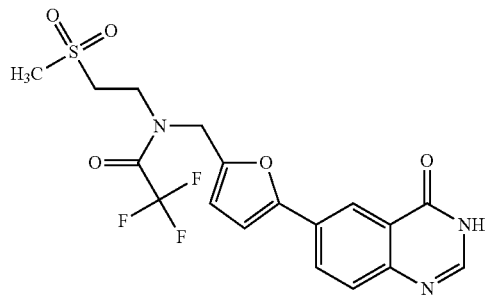 [SMILES: CS(=O)(=O)CCN(Cc1ccc(-c2ccc3nc[nH]c(=O)c3c2)o1)C(=O)C(F)(F)F]

The key compound of formula (IV), according to step c) of the present invention is converted into a compound of formula (V). The preferred compound of formula (V) is that in which X is chlorine since, in comparison to the compounds wherein X is e.g. Br, I, or O-Ms, it has a lower molecular weight, furthermore, it is possible to prepare it more easily and its preparation is less expensive since it uses very inexpensive chlorination reagents such as, e.g., thionyl chloride, phosphoxychloride (i.e. phosphorus oxychloride) and oxalyl chloride.

According to a particularly preferred embodiment the process of the present invention for the preparation of Lapatinib is carried out using compounds wherein R is trifluoroacetyl and X is Chlorine.

A particularly preferred compound is thus the N-{[5-(4-chloroquinazolin-6-yl)furan-2-yl]methyl}-2,2,2-trifluoro-N-[2-(methylsulphonyl)ethyl]acetamide having the following structural formula (V; R=CF$_3$(CO), X=Cl):

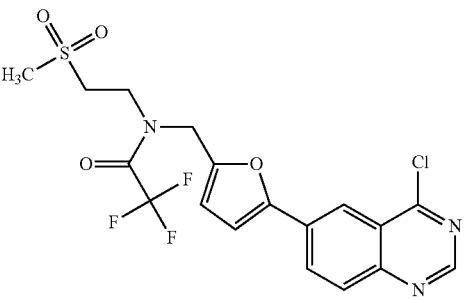

(V; R = CF$_3$(CO), X = Cl)

The N-trifloroacetylated Lapatinib having the following structural formula (VII, R=CF$_3$(CO)):

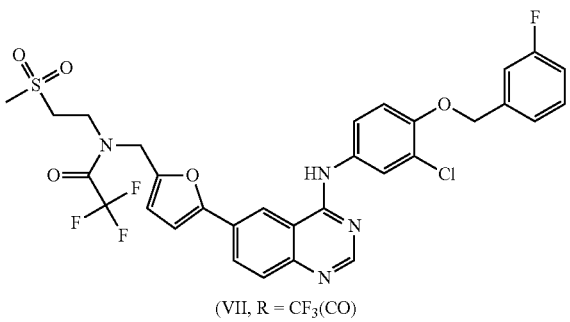 [SMILES: CS(=O)(=O)CCN(Cc1ccc(-c2ccc3ncnc(Nc4ccc(OCc5cccc(F)c5)c(Cl)c4)c3c2)o1)C(=O)C(F)(F)F]

(VII, R = CF$_3$(CO)

is this another particularly preferred compound of the present invention.

In general, the particularly preferred processes and the related intermediates of the present invention are those in which R is trifluoroacetyl.

The compound of formula (III), derived from step a) of the present invention can be conveniently isolated as a sulphate salt having the following structural formula (III; H₂SO₄):

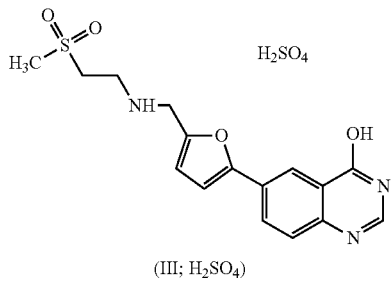 [SMILES: CS(=O)(=O)CCNCc1ccc(-c2ccc3ncnc(O)c3c2)o1 ; "H2SO4"]

(III; H₂SO₄)

The related tautomeric form is also reported:

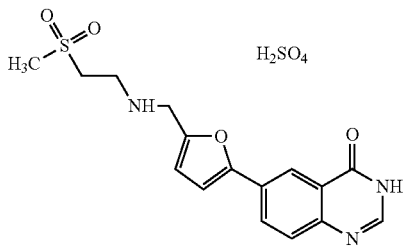 [SMILES: CS(=O)(=O)CCNCc1ccc(-c2ccc3nc[nH]c(=O)c3c2)o1 ; "H2SO4"]

Said solid form is particularly preferred because, unlike other salts of the compound of formula (III) it has a crystalline form, it is easily filterable and allows the attainment of particularly higher yields, even quantitative for step (a). This is due to the complete insolubility or very poor solubility of said salt in the solvent selected to perform the isolation of said salt.

Is not necessary to isolate all the intermediates involved in the present synthetic process.

Indeed, according to one preferred embodiment it is convenient not to isolate the intermediates of formula (V) and (VII) so that it is possible to pass directly in one-pot from the intermediate of formula (IV) to Lapatinib free base or a salt thereof, preferably to the ditosylate salt or to the ditosylate monohydrate salt.

The following compounds are therefore intermediates of the Lapatinib synthetic process according to the present invention:

(a) N-protected-6-[5-({[2-(methylsulphonyl)ethyl] amino}methyl)furan-2-yl]quinazolin-4-ole of formula (IV):

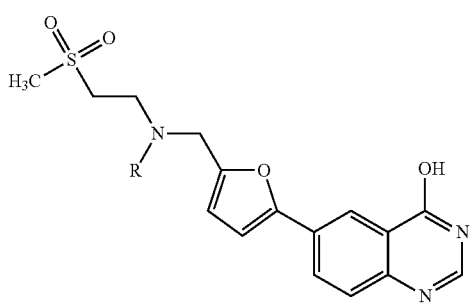

wherein R has the same meaning as described in step (b);

(b) N-protected-N-{[5-(4-substituted-quinazolin-6-yl)furan-2-yl]methyl}-2-(methylsulphonyl) ethanamine of formula (V):

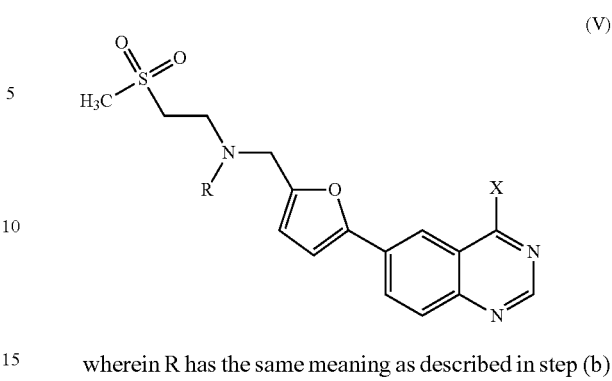

wherein R has the same meaning as described in step (b) and X is chosen from the group consisting of Fluorine, Chlorine, Bromine, Iodine, O-Ms (mesylate), O-Ts (tosylate), O-Tf (triflate), ethanesulfonate (esylate), benzenesulfonate (besylate), p-bronlobenzenesulfonate (brosylate), p-nitrobenzenesulfonate (nosylate);

(c) N-protected Lapatinib of formula (VII):

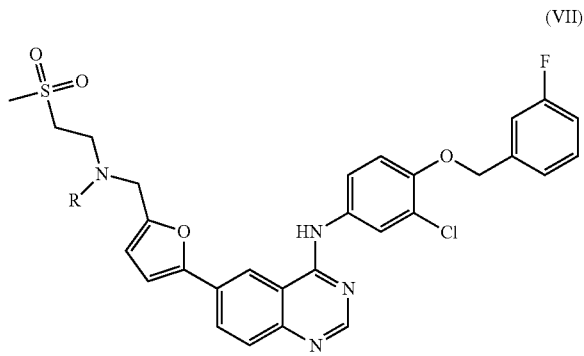

wherein R has the same meaning as described in step (b);

(d) N-protected-2-(methylsulphonyl)-N-({5-[4-(tetrahydro-2H-pyran-2-yloxy)quinazolin-6-yl]furan-2-yl}methyl)ethanamine of formula (III-bis):

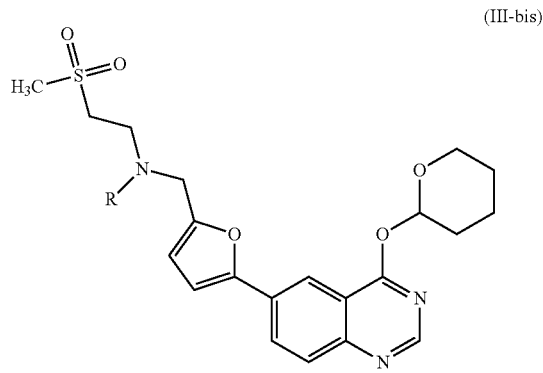

wherein R has the same meaning as described in step (b);

As already mentioned, the preferred compounds from those listed above are those in which R is trifluoroacetyl, Thus the compound 6-[5-({[2-(methylsulphonyl)ethyl] amino}methyl)furan-2-yl]quinazolyn-4-ol sulphate salt of formula (III—H₂SO₄):

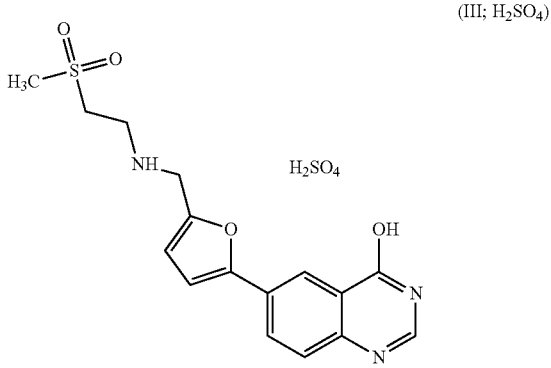 [SMILES: CS(=O)(=O)CCNCc1ccc(-c2ccc3ncnc(O)c3c2)o1 ; "H2SO4"]

(III; H₂SO₄)

is also useful both for the preparation of the compound of formula (IV) and for the preparation of Lapatinib and salts thereof.

All five compounds listed above are thus useful for the preparation of Lapatinib of formula (I) and salts thereof.

The process of the present invention can allow the preparation of Lapatinib base or conveniently, can allow the preparation of Lapatinib ditosylate and/or Lapatinib ditosylate monohydrate.

The starting compound 2-(methylsulphonyl)-N-({5-[4-(tetrahydro-2H-pyran-2-yloxy)quinazolin-6-yl]furan-2-yl}methyl)ethanamine of formula (II):

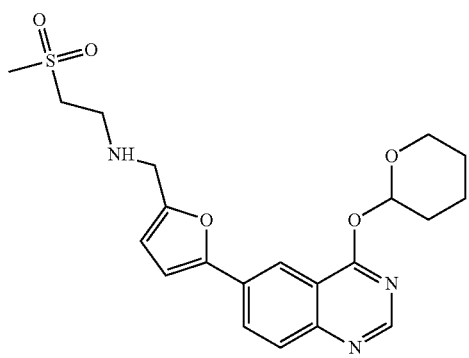

(II)

is prepared as described in the experimental section.

In one embodiment, step (a) in the preparation of the intermediate 6-[5-({[2-(methylsulphonyl)ethyl]amino}methyl)furan-2-yl]quinazolyn-4-ol of formula (III):

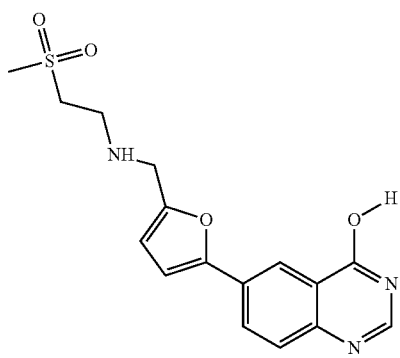

(III)

by means of deprotection of the intermediate 2-(methylsulphonyl)-N-({5-[4-(tetrahydro-2H-pyran-2-yloxy) quinazolin-6-yl]furan-2-yl}methyl) ethanamine of formula (II) can be conveniently carried out in an organic solvent such as an alcohol, for example in Methanol, or in acetonitrile and in presence of a reactive acid such as, e.g. sulphuric acid, methanesulphonic acid or para-toluenesulphonic acid. The reaction is carried out at room temperature for at least one hour providing molar yields of around 95%. In one preferred form, the reaction can also be conveniently carried out in the presence of sulphuric acid, in methanol at 40° C. In said case the yield is greater than 95%.

The product of formula (III) can be isolated as a base or as a sulphate salt. In the case where the sulphate salt is isolated, the overall yield of this step can also be quantitative.

In one preferred embodiment, step (b) can also be carried out using trifluoroacetic anhydride in dimethylformamide as solvent. Triethylamine, which works as a base, is also used and the reaction is typically carried out at 25° C.

The typical molar yield for step (b) is between 80% and 92% in the case of starting from the free base of compound (III).

In one preferred embodiment, step (c) for conversion of the intermediate of formula (IV) to give the N-protected-N-{[5-(4-substituted-quinazolin-6-yl) furan-2-yl]methyl}-2-(methylsulphonyl)ethanamine of formula (V):

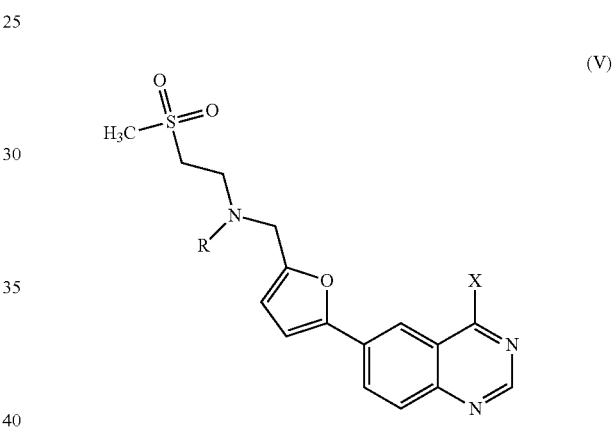

(V)

in which R has the same meanings as described in step (b) and X is selected in the group consisting of Fluorine, Chlorine, Bromine, Iodine, O-Ms (mesylate), O-Ts (tosylate), O-Tf (triflate), ethanesulfonate (esylate), benzenesulfonate (besylate), p-bromobenzenesulfonate (brosylate), p-nitrobenzenesulfonate (nosylate); is carried out in an organic solvent, typically in toluene, or acetonitrile or dioxane, dioxane and acetonitrile being preferred. The most preferred solvent is dioxane because it allows performing all the following steps avoiding unwanted phase-separations, allowing optimal solubilisation of the reagents and the ability to heat at higher temperatures in comparison to acetonitrile for example. This allows short-time reactions and this is an advantage with reference to the timing of the production cycle.

In said step, reagents able to halogenate must be used, such as for example POCl₃, SOCl₂, (COCl)₂ and PBr₃ or by using sulphonyl halides and sulphonic anhydrides such as for example mesylchloride, tosylchloride, tosyl anhydride and triflyc anydride.

In one preferred embodiment, step (c) for the preparation of the intermediate of formula (V) in which X is chlorine is carried out in dioxane using phosphorous oxychloride (POCl₃) in the presence of a base such as for example triethylamine (TEA). Other chlorinating agents can alternatively be used such as thionyl chloride or oxalyl chloride, phosphorous oxychloride being preferred.

The reaction is carried out at 80° C.

In one preferred embodiment, the product from step (c) is not isolated as a solid but is directly subjected to the reaction of step (d).

In one preferred embodiment, step (d) for the preparation of the N-protected Lapatinib of formula (VII):

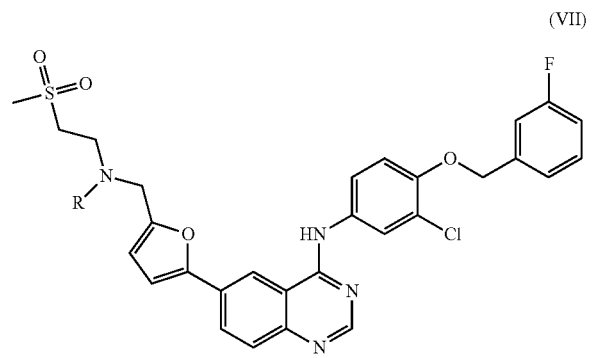

(VII)

by means of a coupling reaction of the intermediate of formula (V) with 3-chloro-4-[(3-fluorobenzyl)oxy]aniline of formula (VI):

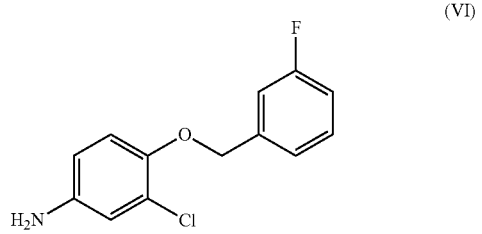 [SMILES: Nc1ccc(OCc2cccc(F)c2)c(Cl)c1]

(VI)

can be conveniently carried out in an organic solvent, preferably in a non-polar solvent such as toluene or in Acetonitrile or, more preferably in Dioxane, being the preferred solvent used in the previous step. The reaction is typically carried out at a temperature comprised between 60° C. and 75° C., with a temperature of 60° C. being preferred. The reaction duration is approx. one hour.

The compound of formula (VII) can be isolated but, according to one preferred embodiment, it is converted in one-pot to Lapatinib, or, even more preferably, it is directly converted to Lapatinib ditosylate or Lapatinib ditosylate monohydrate.

Step (e) can be carried out by means of the addition of an aqueous solution of potassium carbonate to the dioxane organic phase containing said intermediate of formula (VII). Maintaining the system at 80-85° C., in the case wherein R is trifluoroacetyl, the reaction is completed in approx. two hours.

According to one particularly preferred embodiment of the invention the compound of formula (IV) is converted into Lapatinib ditosylate monohydrate without isolating any intermediates. The examples report the experimental procedure for obtaining Lapatinib ditosylate and its conversion to monohydrate. The molar yield for the entire process, including a further recrystallization step of the monohydrate product, is comprised between 47 and 71%, thus producing at the end a product having high pharmaceutical quality (HPLC Purity >99.90% (A %) with each impurity less than 0.05% (A %)).

In one embodiment, the preparation of Lapatinib ditosylate monohydrate can be carried out by first obtaining Lapatinib ditosylate and then subjecting said compound to a hydration reaction in water. Said methods for the preparation of Lapatinib ditosylate monohydrate are known in the literature.

The compounds of the present invention having the tetrahydropyranyl group, such as for example the compounds of formula (II) or (III-bis) are highly soluble in organic solvents, thus making them particularly interesting for industrial applications since they allow working in much more concentrated solutions in comparison to the intermediates used in the current industrial synthesis of Lapatinib according to the description in U.S. Pat. No. 7,157,466. This offers the possibility of production processes having much lager product batch size.

The process of the present invention makes it possible to obtain Lapatinib, and in particular Lapatinib ditosylate monohydrate in high yields, with a synthetic process composed of highly selective and clean reactions, and is easily industrially scalable. Furthermore, according to the preferred aspects it is possible to avoid the isolation of various intermediates making it possible to avoid wasting time due to the drying of the intermediate products and making it possible to perform the entire process in a few synthetic steps with obvious effects on the economy of the entire process. The overall process has high yields.

According to a preferred embodiment of the invention step a-bis and step b-bis can be carried out one-pot, i.e. avoiding the isolation of the compound of formula (III-bis). It has been indeed found that performing the step a-bis with an anhydride or an acyl halide the whole process comprising steps a-bis and b-bis car be performed without any other reagent such as for instance a base and avoiding the isolation of the compound (III-bis). In the case in which, e.g. the preferred trifluoroacetic anhydride is employed, no other reagents (except the solvent medium) are necessary. It has been in fact discovered that the acid delivered during the reaction of nitrogen protection in step a-bis is able to promote the cleavage of the tetrahydropiranyl group in the following step b-bis. It has been also observed that while the acetylation reaction is extremely fast and complete already at room temperature, the following removal of the piranyl group requires high temperatures and longer times. Thus, it has been understood that the intermediate of formula (II) is completely converted to the intermediate of formula (III-bis, R=CF$_3$(CO)) before that this intermediate begin to leave his tetrahydropiranyl protection. In other words, no traces intermediate of formula (III) are observed during the combined steps a-bis and b-bis.

After the complete formation of intermediate (III-bis), also a different acid, such as sulphoric acid, could be added to facilitate the cleavage of the tetraidropiranyl group, although it is not necessary.

According to a preferred embodiment of the invention step a-bis and b-bis are carried out one-pot by means of trifluoroacetic anhydride.

The steps a-bis and b-bis can be carried out in presence of an organic solvent such as acetonitrile, dichloromethane, toluene, tetrahydrofuran, dioxane and dimethylformide, being preferred dimethylformamide and dioxane since they allow to increase the molar yield and purity of the reaction. Furthermore, they allow to reach higher temperature in comparison with other solvents, thus shortening the reaction time.

In a preferred embodiment, steps a-bis and b-bis are carried out one-pot with trifluoroacetic anhydride in dioxane.

It is convenient to perform steps a-bis and b-bis in absence of water, e.g. with a K.F. value lower than 1000 ppm, since water consumes the acetylating reactant.

The acetylation reaction of step a-bis is thus performed at room temperature being instantaneous. The deprotection reaction of step b-bis instead requires high temperature such as 90-95° C. and is typically completed in 3 hours.

Operating in this way, it is possible to avoid the isolation of the compound of formula (II-bis) and only one reagent is employed to perform both steps with consequent advantage for the economy of the process.

Figure 2:
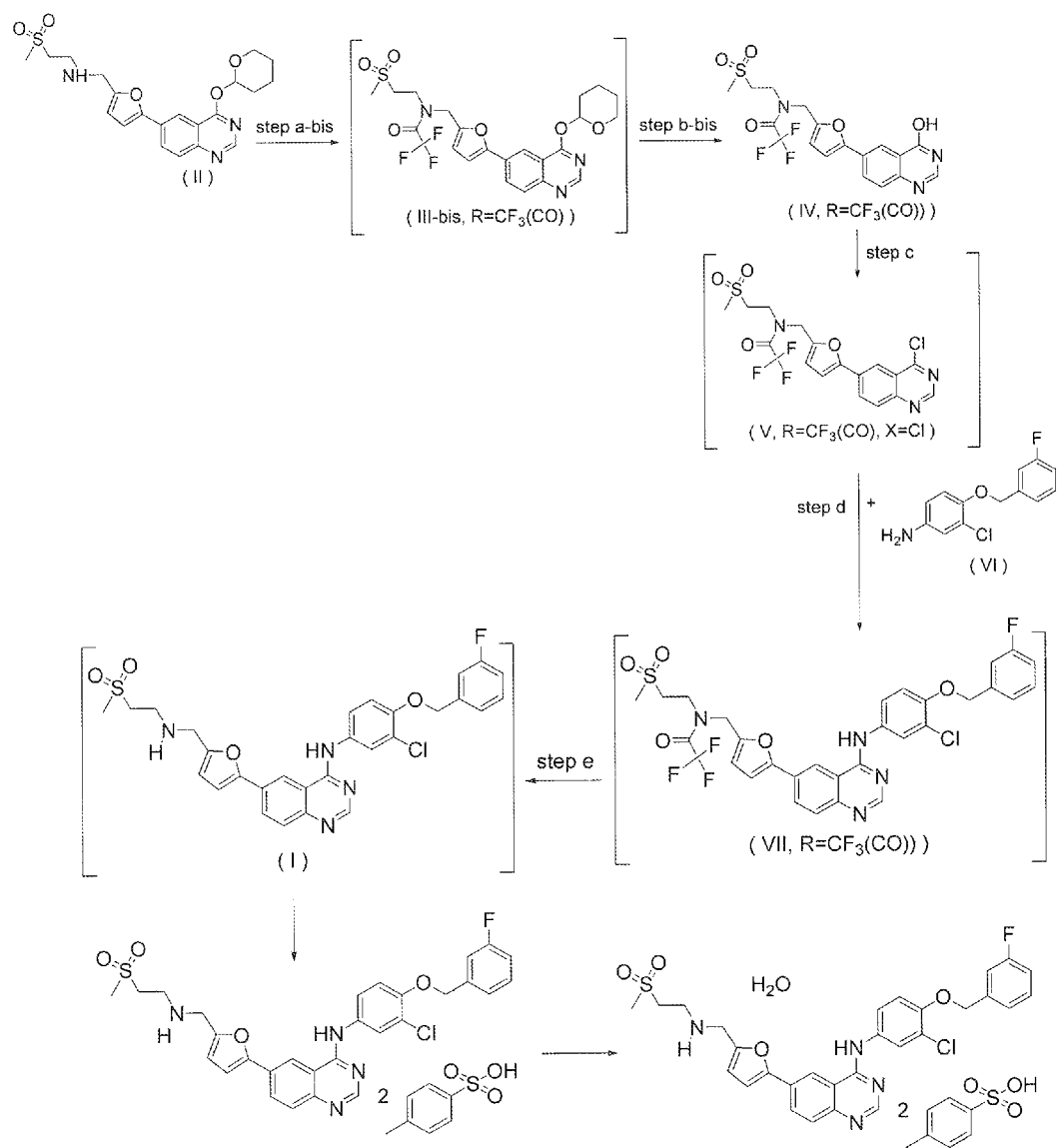
FIG. 2 shows the scheme of the process for the synthesis of Lapatinib according to a preferred embodiment of the present invention.

According to the process of the present invention, considering also the preferred embodiment of performing one-pot the steps a-bis and b-bis, Lapatinib ditosilate anhydrous is prepared from the compound of formula (II) in just two steps isolating only the compound of formula (IV). The FIG. 2 shows the process of synthesis of Lapatinib according a preferred embodiment of the present invention.

The molar yield of the whole process starting from the compound of formula (II) is very high since the molar yield of steps a-bis and b-bis carried out one-pot to the compound of formula (IV) is about 90%, the step of conversion one-pot of the compound (IV) to Lapatinib ditosilate anhydrous is about 70% and the conversion of this to Lapatinib ditosilate monohydrate is practically quantitative, thus the overall molar yield is about 60-65%, which is much higher in comparison with the known processes for the preparation of Lapatinib ditosilate monohydrate. This is obviously beneficial for the process and the product from the economic point of view.

EXPERIMENTAL PART

Example 1

Preparation of the Intermediate 6-iodo-4-(tetrahydro-2H-pyran-2-yloxy)quinazoline Synthetic scheme

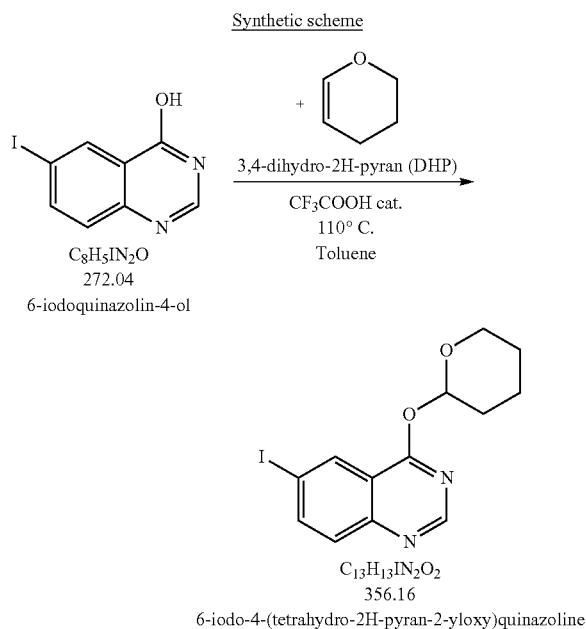

Under an atmosphere of nitrogen, a glass 4-necked round bottom flask (RBF) fitted with a mechanical stirrer, condenser and thermometer was loaded with 30 g of 6-Iodoquinazolyn-4-ol (110 mmol), 300 mL of Toluene anhydrated on molecular sieves, 1.26 g (0.84 mL) of trifluoroacetic acid (0.1 mol. equiv.) and 79.4 g (80 mL) of 3,4-dihydro-2H-pyran (DHP) (944 mmol; 8.6 mol. equiv.). The mixture is mixed at reflux (T=110-115° C.) for 2-3 hours and the reaction is monitored by TLC using Hexane/Ethyl Acetate (2:8) as eluent. When the reaction has gone to completion, a homogeneous solution is obtained which is cooled to room temperature and washed with 2×120 mL of a saturated sodium chloride solution. The organic phase was concerted to residue under vacuum at an external T of 40-45° C.

The product was recrystallized by adding 150 mL of Ethyl acetate and heating at reflux. The mixture was cooled to room temperature and stirred for 30 minutes and was then cooled to 0-5° C. and stirred for 30 minutes.

The slurry was filtered and the solid washed with 60 mL of Ethyl acetate pre-chilled to 0-5° C. The product was dried under vacuum at 40° C. for 6-8 hours, thus giving 28.6 g of product as a white crystalline solid with a molar yield of 72.8%.

$^1$H-NMR (400 MHz, dmso-d$_6$): 1.75 (m, 6H, CH$_2$(THP)); 3.69 (dt, J=11.6, 2.9 Hz, 1H, CH$_2$O (THP)); 4.11 (app. d, J=11.6 Hz, 1 H, CH$_2$O (THP)); 5.85 (dd, J=8.7, 4.2 Hz, 1H, OCHO(THP)); 7.50 (d, J=8.5 Hz, 1 H, H-8); 8.16 (dd, J=8.5, 1.5 Hz, 1H,H-7); 8.45 (d, J=1.8 Hz, 1H, H-5); 8.45 (s, 1H, H-2).

Example 2

Preparation of the Intermediate 5-[4-(tetrahydro-2H-pyran-2-yloxy)quinazolin-6-yl]furan-2-carbaldehyde Synthetic scheme

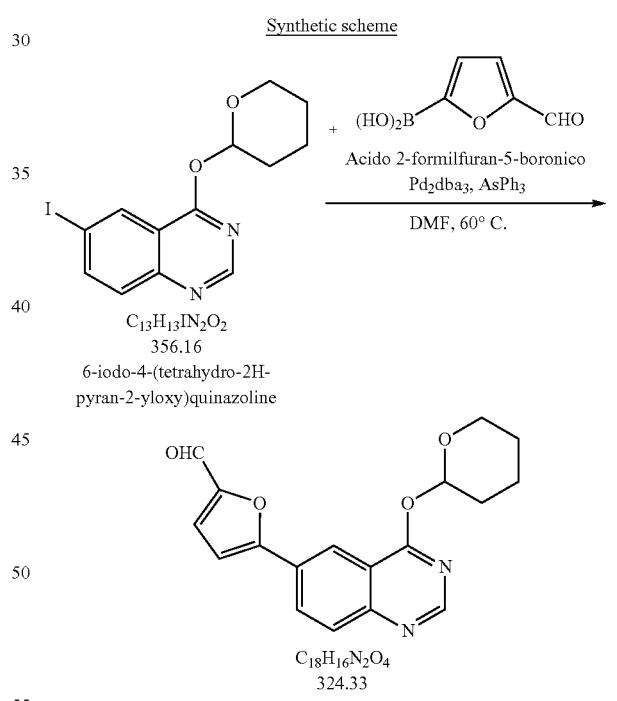

Under an atmosphere of nitrogen, a glass 4-necked round-bottom flask equipped with a mechanical stirrer, condenser and thermometer, all of them previously anhydrated, was loaded with 320 mg of Palladium trisdibenzylidenacetone (Johnson-Mathey—Pd-94; 1.25% mol.) weighed under nitrogen, 430 mg of Triphenylarsine (Aldrich) (0.025 mol. equiv.). 200 mL of anhydrous DMF previously degassed under nitrogen for 1 hour were added. The mixture was stirred for 10-15 minutes at room temperature then 15.5 g of Potassium carbonate (2 mol. equiv.) and 10.2 g of 2-formylfuran-5-boronic acid (1.3 mol. equiv.) are added and, finally, 20.0 g of 6-iodo-4-(tetrahydro-2H-pyran-2-yloxy)quinazoline. The reaction mixture is heated for 2 hours at 60-65° C. The reaction can be monitored by means of TLC using Hexane/AcOEt (6:4) as eluent.

When the reaction has gone to completion, 200 mL of purified water were added and the mixture was extracted with 2×500 mL of Dichloromethane. The phases were separated and the aqueous phase was washed with 2×300 mL of 5% NaHCO$_3$, then with 2×300 mL of saturated sodium chloride solution. The organic phase was then anhydrated with anhydrous sodium sulphate then with 2.0 g of Acticarbon and filtered through a dicalite panel, which was then washed with 2×100 mL of dichloromethane.

The solution was washed and concentrated to residue under vacuum at an external temperature of 35-40° C. The residue, a yellow/orange solid, was taken up with 200 mL of AcOEt, then stirred at 20-25° C. for 30 minutes and then cooled to 0-5° C. and stirred for a further 30 minutes. The slurry was filtered and the solid was washed with 80 mL of AcOEt pre-chilled to 0-5° C. The solid was dried in an oven at 35-40° C. for 4-5 hours. 13.5 g of product were thus obtained corresponding to a molar yield of 74.1%.

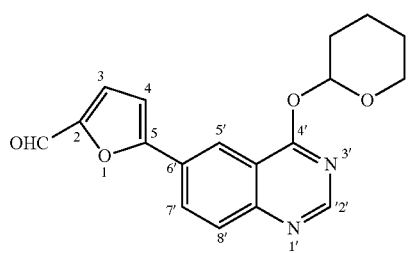

$^1$H-NMR (400 MHz, dmso-d$_6$): 1.77 (m, 6H, CH$_2$(THP)); 3.73 (dt, J=11.6, 2.7 Hz, 1H, CH$_2$O (THP)); 4.13 (app. dd, J=11.0, 1.6 Hz, 1 H, CH$_2$O (THP)); 5.90 (dd, J=8.2, 4.6 Hz, 1H, OCHO(THP)); 7.53 (d, J=3.7 Hz, 1 H, CH(furan)); 7.72 (d, J=3.7 Hz, 1H, CH(furan)); 7.84 (d, J=8.6 Hz, 1H, H-8'); 8.48 (dd, J=8.5, 1.9 Hz, 1H,H-7'); 8.51 (s, 1H, H-2'); 8.59 (d, J=1.6 Hz, 1H, H-5'); 9.68 (s, 1H, CHO).

Example 3

Preparation of the Intermediate 2-(methylsulphonyl)-N-({5-[4-(tetrahydro-2H-pyran-2-yloxy)quinazolin-6-yl]furan-2-yl}methyl)ethanamine Synthetic scheme

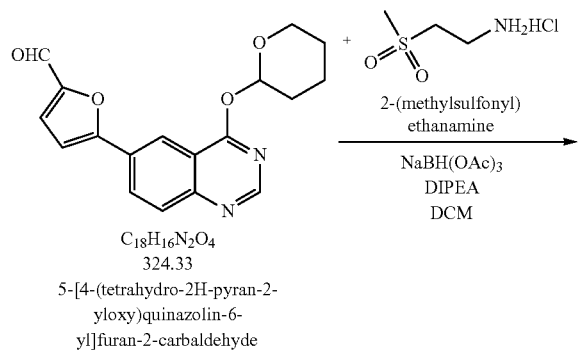

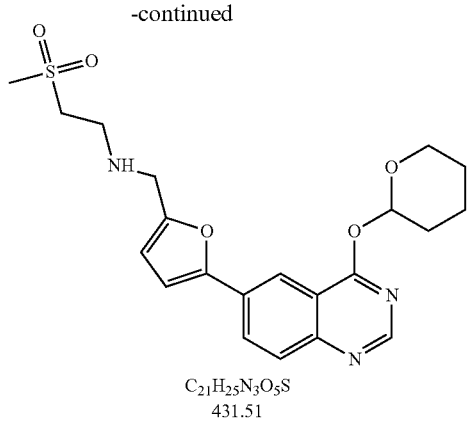

C$_{21}$H$_{25}$N$_3$O$_5$S
431.51
2-(metilsulphonil)-N-({5-[4-(tetrahydro-2H-pyran-2-yloxy)quinazolin-6-yl]furan-2-yl}methyl)ethanamine Under an atmosphere of nitrogen, 1.0 g of 5-[4-(tetrahydro-2H-pyran-2-yloxy)quinazolin-6-yl]furan-2-carbaldehyde and 20 mL of anhydrous dichloromethane, as dried previously, have been loaded into a 4-necked, glass round-bottomed flask fitted with a mechanical stirrer, condenser and thermometer. 0.73 g of 2-(methylsulphonyl)ethanamine hydrochloride (1.5 mol. equiv.) and 0.60 g (0.80 mL) of Diisopropylethylamine (DIPEA) (1.5 mol. equiv.) are added at a temperature of 20-25° C. The reaction mixture is stirred for 30 minutes at 30-35° C. then cooled to 20-25° C. and 1.31 g of sodium triacetoxyborohydride (Aldrich) (2.0 mol. equiv.) added. The reaction mixture is stirred at 20-25° C. for 2 hours and then the conversion checked by TLC, using a hexane/ethyl acetate mixture (6:4) as eluent, On completion of the reaction, 10 mL of a saturated solution of sodium bicarbonate are added and the phases separated. The organic phase is anhydrated over anhydrous sodium sulphate and then concentrated to residue under vacuum at an external temperature of 35-40° C. The product is dried under high vacuum (using an Edwards pump). 1.06 g of product is obtained, corresponding to a molar yield of 80%.

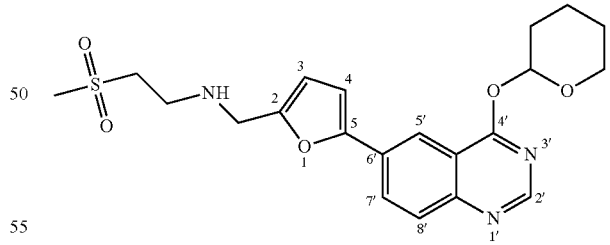

$^1$H-NMR (400 MHz, dmso-d$_6$): 1.86 (m, 6H, CH$_2$(THP)); 2.99 (t, J=6.6 Hz, 2 H, —SO$_2$CH$_2$CH$_2$NH—); 3.05 (s, 3H, CH3); 3.28 (t, J=6.6 Hz, 2 H, —SO$_2$CH$_2$CH$_2$NH—); 3.71 (dt, J=11.8, 2.9 Hz, 1H, CH$_2$O (THP)); 3.83 (s, 2 H, —NH—CH$_2$-furan); 4.12 (app. d, J=11.0, 1 H, CH$_2$O(THP)); 5.90 (dd, J=8.8, 4.4 Hz, 1H, OCHO(THP)); 6.46 (d, J=3.2 Hz, 1 H, CH(furan)); 7.10 (d, J=3.2 Hz, 1 H, CH(furan)); 7.74 (d, J=8.6 Hz, 1H, H-8'); 8.17 (dd, J=8.5, 2.0 Hz, 1H, H-7'); 8.38 (d, J=1.8 Hz, 1H, H-5'); 8.43 (s, 1H, H-2').

Example 4

Preparation of the Intermediate 6-[5-({[2-(methylsulphonyl)ethyl]amino}methyl)furan-2-yl]quinazolin-4-ol of Formula (III) (as Free Base)

Synthetic scheme

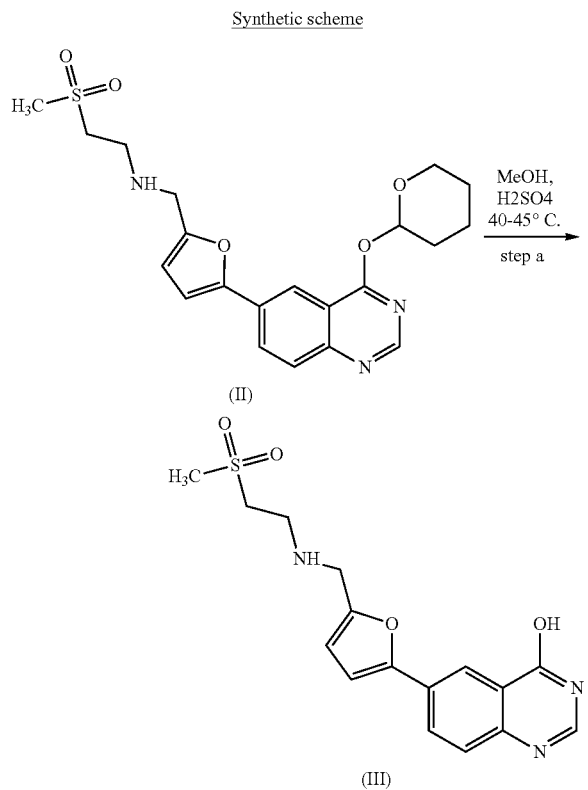

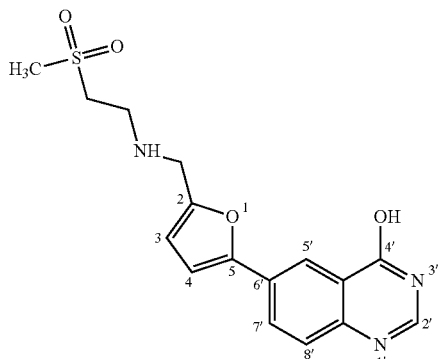

$^1$H-NMR spectrum:

$^1$H-NMR (400 MHz, dmso-d$_6$): 2.98 (t, J=6.6 Hz, 2 H, —SO$_2$CH$_2$CH$_2$NH—); 3.04 (s, 3 H, CH$_3$); 3.28 (t, J=6.6 Hz, 2 H, —SO$_2$CH$_2$CH$_2$NH—); 3.82 (s, 2 H, —NH—CH2-furan); 6.46 (d, J=3.3 Hz, 1 H, CH(furan)); 7.07 (d, J=3.3 Hz, 1 H, CH(furan)); 7.71 (d, J=8.6 Hz, 1H, H-8'); 8.07 (s, 1H, H-2'); 8.13 (dd, J =8.6, 2.2 Hz, 1H, H-7'); 8.35 (d, J=2.0 Hz, 1H, H-5'); 12.35 (s, 1H, amide).

Into a glass round-bottomed flask fitted with a condenser, thermometer, mechanical stirrer and nitrogen feed, are added (under an atmosphere of nitrogen) 106.4 g (1 equiv.) of 2-(methylsulphonyl-N-({5-[4-(tetrahydro-2H-pyran-2-yloxy)quinazolin-6-yl]furan-2-yl}methyl) ethanamine of formula (II), obtained in the form of an oil in accordance with example 3 at a suitable scale.

720 mL (6.8 V) of methanol are added. The reaction mixture is heated to 40-45° C. and over a period of 30 minutes, a solution of 48.4 g, equal to 26.3 mL (2 equiv.) of concentrated sulphuric acid (MW=98.09, d=1.84 g/mL) in 80 mL (0.8 V) of methanol, is added. The reaction mixture is stirred at 40-45° C. for at least 2 hours, and the conversion monitored by HPLC. If the reaction has gone to completion, 700 mL (6.6 V) of purified water, at a temperature of 40-45° C., are added. The pH is adjusted to a value of between 6-7 using a pH meter and as much 15% sodium hydroxide as required. Approx. 700 ml of solvent are distilled under vacuum at 40-45° C. This is stirred for 0.5 h at 20-25° C. and then cooled to 0-5° C. and stirred for at least 2 h, then filtered. The panel is washed with 80 mL (1 V) of cold purified water and then washed again with 2×40 mL (2×0.5 V) of a water/methanol mixture (50/50), pre-chilled to 0-5° C., and then dried in an oven at 40° C. for 5-6 h. 86.6 g of product (K.F.=9.0%) are obtained, equal to a molar yield of 92%. The HPLC purity A/A % is 97-98%.

Example 5

Preparation of the Intermediate 6-[5-({[2-(methylsulphonyl)ethyl]amino}methyl)furan-2-yl]quinazolin-4-ol sulphate Salt of Formula (III—H$_2$SO$_4$)

Synthetic scheme

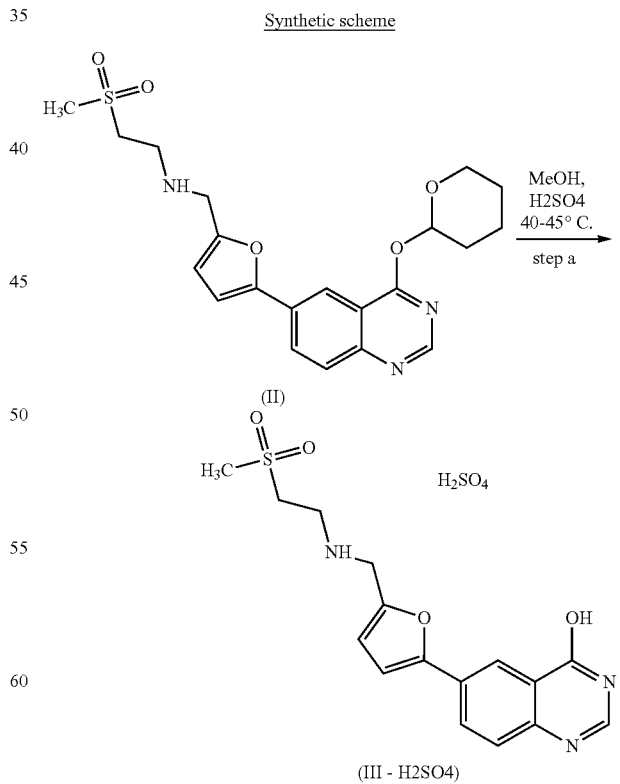

Into a glass round-bottomed flask fitted with a condenser, thermometer, mechanical stirrer and nitrogen feed, are added (under an atmosphere of nitrogen). 106.4 g (1 equiv.) of 2-(methylsulphonyl-N-({5-[4-(tetrahydro-2H-pyran-2-yloxy) quinazolin-6-yl]furan-2-yl}methyl) ethanamine of formula (II), obtained in the form of an oil in accordance with example 3 at a suitable scale. 720 mL (6.8 V) of methanol are added. The reaction mixture is heated to 40-45° C. and over a period of 30 minutes, a solution of 48.4 g, equal to 26.3 mL (2 equiv.) of concentrated sulphuric acid (MW=98.09, d=1.84 g/mL) in 80 mL (0.8 V) of methanol, is added. The reaction mixture is stirred at 40-45° C. for at least 2 h, and the conversion monitored by HPLC. If the reaction has gone to completion, it is cooled to a temperature of 20-25° C., and stirred for 1 h. It is then filtered by washing with 2×53 mL (2×0.5 V) of methanol. 110 g of product are obtained, equal to a quantitative molar yield. HPLC purity A/A % 97-98%.

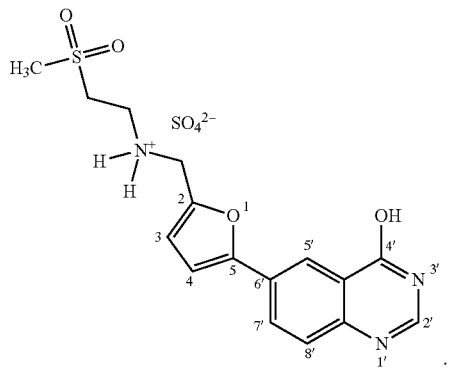

$^1$H-NMR (400 MHz, dmso-d$_6$): 3.16 (s, 3 H, CH$_3$); 3.46-3.44 (m, 2 H, —SO$_2$CH$_2$CH$_2$NH$_2^+$-); 3.59-3.55 (m, 2 H, —SO$_2$CH$_2$CH$_2$NH$_2^+$-); 4.46 (s, 2 H, —$^+$NH$_2$—CH$_2$-furan); 6.83 (d, J=3.4 Hz, 1 H, CH(furan)); 7.23 (d, J=3.4 Hz, 1 H, CH(furan)); 7.78 (d, J=8.6 Hz, 1H, H-8'); 8.24 (dd, J=8.6, 2.1 Hz, 1H, H-7'); 8.29 (s, 1H, H-2'); 8.51 (d, J=2.0 Hz, 1H, H-5'); 9.27 (br s, 1H, NH$_2^+$).

Example 6

Preparation of the Intermediate 2,2,2-trifluoro-N-{[5-(4-hydroxyquinazolin-6-yl)furan-2-yl]methyl}-N-[2-(methylsulphonyl)ethyl]acetamide of Formula (IV, R=CF$_3$(CO))—Exemplifying the Invention Synthetic scheme

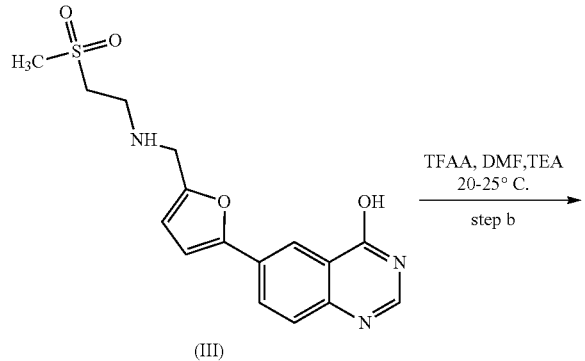

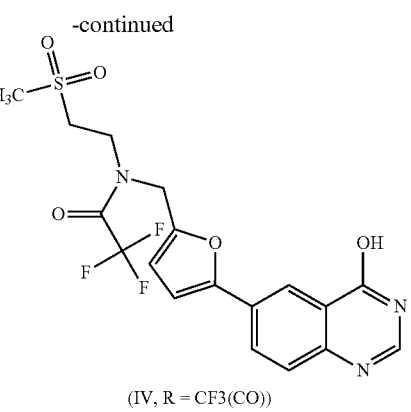
(IV, R = CF3(CO))

80 g (1 equiv.) of 6-[5-({[2-(methylsulphonyl)ethyl]amino}methyl)furan-2-yl]quinazolin-4-ol of formula (III) (K.F. 9.0%) are loaded into a flask. The mixture is then subjected to azeotropic distillation to residue three times using heptanes (3×800 mL, 3×10 V) in order to remove the water, until a product is obtained with KF<0.5%. The solid residue produced is loaded into a glass flask fitted with a condenser, thermometer, mechanical stirrer, addition funnel and nitrogen inlet. 400 mL (5 V) of DMF and 42.4 g equal to 58.4 mL (2.0 equiv.) of triethylamine (MW=101.19 d=0.726 g/mL) are added, and 66.0 g equal to 44.4 mL (1.5 equiv.) of trifluoroacetic anhydride (MW=210.03, d=1.487 g/mL) are added with caution while maintaining the temperature at 20-25° C. (using a dropping funnel). On completion of addition, the mixture is stirred at 20-25° C. for 1 hour. The conversion is monitored by HPLC. If the reaction has gone to completion, 800 mL (10 V) of purified water are added with caution. The reaction mixture is stirred at 20-25° C. for 30 minutes and then cooled to 0-5° C. and stirred for 2 hours.

The mixture is filtered washing the solid with 160 mL (2 V) of chilled purified water. The product is then washed further using 2×160 mL (2×2 V) of chilled methanol denatured ethanol. This is then dried under vacuum at T max 40° C. for at least 5-6 h. 85.5 g of product are obtained, equal to a molar yield of 92%. The HPLC purity A/A % is 98-98.5%. $^1$H-NMR spectrum:

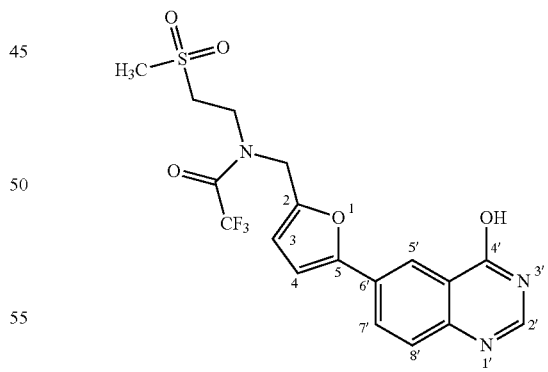

$^1$H-NMR (400 MHz, dmso-d$_6$): the NMR spectrum at room temperature reveals the presence of two N—COCF$_3$ bond rotamers in a ratio of approx. 2:1.3.07 (s, 3 H, CH$_3$, maj. rot.); 3.10 (s, 3 H, CH$_3$, min. rot.); 3.48-3.44 (m, 2 H, —SO$_2$CH$_2$CH$_2$NCO—, maj. rot.); 3.68-3.65 (m, 2 H, —SO$_2$CH$_2$CH$_2$NCO—, min. rot.); 3.85-3.81 (m, 2 H, —SO$_2$CH$_2$CH$_2$NCO—, maj. rot.); 3.91-3.88 (m, 2 H, —SO$_2$CH$_2$CH$_2$NCO—, min. rot.); 4.82 (s, 2 H, —NH—CH$_2$-furan, min. rot.); 4.86 (s, 2 H, —NH—CH$_2$-furan, min. rot.); 6.64 (d, J=3.3 Hz, 1 H, CH(furan), min. rot.); 6.73 (d, J=3.4 Hz, 1 H, CH(furan), maj. rot.); 7.14 (d, J=3.4 Hz, 1 H, CH(furan), min. rot.); 7.17 (d, J=3.3 Hz, 1 H, CH(furan), maj. rot.); 7.73 (d, J=8.6 Hz, 1H, H-8', min. rot.); 7.74 (d, J =8.6 Hz, 1H, H-8', min. rot.); 8.12 (s, 1H, H-2'); 8.13 (dd, J=8.6, 2.1 Hz, 1H, H-7'); 8.36 (m, 1H, H-5'); 12.36 (br s, 1H, amide).

Example 7

Preparation of Lapatinib Ditosylate According to the Preferred Aspects of the Invention

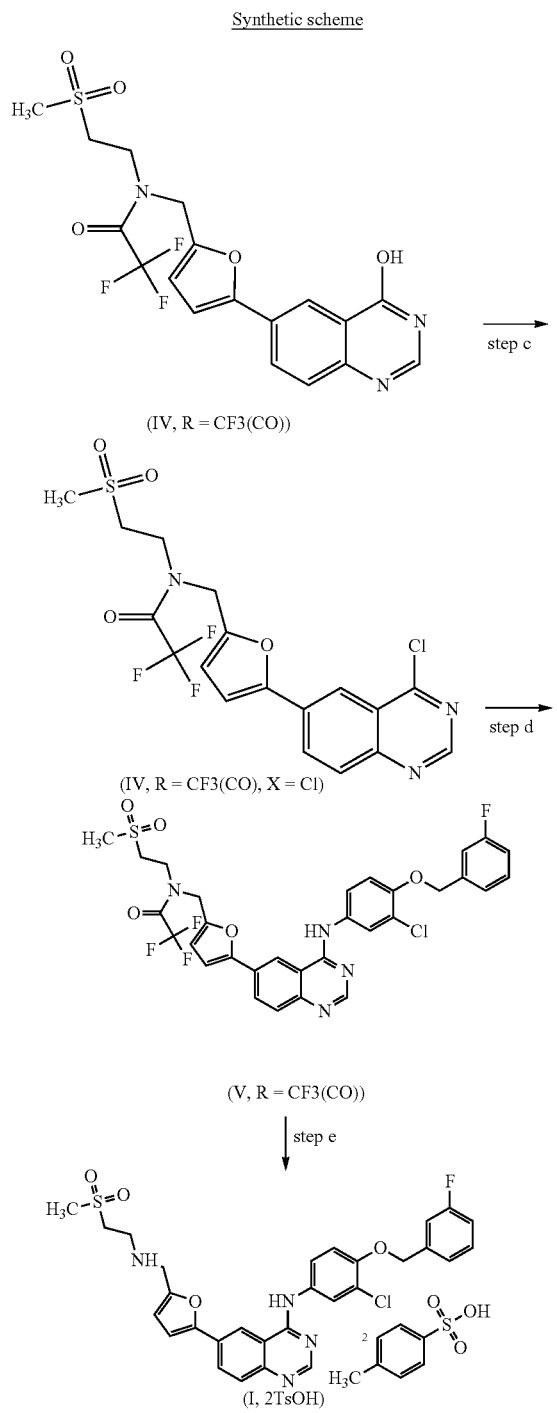

Synthetic scheme

Into a glass flask fitted with a condenser, thermometer, mechanical stirrer, addition funnel and nitrogen inlet are loaded (under an atmosphere of nitrogen) 25 g (1 equiv.) of 2,2,2-trifluoro-N-{[5-(4-hydroxyquinazolin-6-yl) furan-2-yl]methyl}-N-[2-(methylsulphonyl)ethyl]acetamide of formula (IV, R=CF$_3$(CO) and 250 mL (10 V) of dioxane. 17.3 g equal to 10.5 mL (2 equiv.) of phosphorus oxychloride (MW=153.33; d=1.645 g/mL) are added with caution at a temperature of 20-25° C. 11.4 g equal to 15.7 mL (2 equiv.) of triethylamine (MW=101.19; d=0.726 g/mL) are added with caution at a temperature of 20-25° C. On completion of addition, the mixture is allowed to return to room temperature and then stirred at 95-100° C. (reflux) for 1 h. The conversion is monitored by HPLC. If the reaction has gone to completion, the reaction mixture is evaporated to residue in a rotavapor at a max. temperature of 40° C. The residue is then taken up with 250 mL (10 V) of dioxane and evaporated to residue. The residue contains N-{[5-(4-chloroquinazolin-6-yl)furan-2-yl]methyl}-2,2,2-trifluoro-N-[2-(methylsulphonyl)ethyl]acetamide of formula (V; R=CF$_3$(CO), X=Cl).

This is then taken up with 200 mL (8 V) of Dioxane. The preparation is heated to 55-60° C. and over a time of approx. 15 min., a solution of 14.2 g (1.0 equiv.) of 3-chloro-4-[(3-fluorobenzyl)oxy]aniline of formula (VI) (MW=251.68) dissolved in 50 mL (2 V) of dioxane added. The mixture is heated to 55-60° C. and stirred for 1 hour. The conversion is monitored by HPLC. If the reaction has gone to completion, a solution is prepared with 47 g (6 equiv.) of potassium carbonate (MW=138.21) in 250 mL (10 V) of purified water. The potassium carbonate solution is added to the reaction mixture at T=55-60° C.

The reaction mixture is heated to 80-85° C. and stirred for 2 h. The conversion is monitored by HPLC. If the reaction has gone to completion, it is cooled to 20-25° C. The pH is adjusted to >12 using the required quantity of 30% sodium hydroxide. The phases are separated. The aqueous phase is extracted with 250 mL (10 V) of Isopropyl acetate, The organic phase is separated and combined with the previously separated organic phase. The combined organic phases are washed with 125 mL (5 V) of a 10% sodium chloride solution. The combined organic phases are evaporated to residue in a rotavapor at a max. temperature of 40° C. 125 mL (5 V) of DMF (dimethylformamide) are added to the residue.

The preparation is heated to 35-40° C. and 22.5 g (2.1 equiv.) of p-toluenesulphonic acid monohydrate (MW=190.22) added. The preparation is stirred for 1 h at 35-40° C. then cooled to 20-25° C.

It is preferable that crystallization be initiated with 250 mg (1% wt.) of Lapatinib ditosylate. On achieving precipitation, the preparation is cooled to 0-5° C. and stirred for at least 1 h. The preparation is cooled to −15/−10° C. and stirred for 2 h. The panel is filtered and washed with 12.5 mL (0.5 V) of DMF chilled to −10/−5° C. The wet product is removed and taken up with 125 mL (5 V) of DMF. The preparation is heated to 40-45° C. and stirred at said T for 1 h. The preparation is cooled spontaneously to 20-25° C. and stirred for 1 h. The preparation is cooled to 20-25° C. and stirred for 1 h. The preparation is cooled to 0-5° C. and stirred for 1 hour. The preparation is cooled to −15/−10° C. and stirred for 2 h.

The preparation is filtered washing the solid with 2×12.5 mL (2×0.5 V) of DMF pre-chilled to −15/−10° C. The solid is dried at 70° C. under vacuum for at least 10 hours. 37.0 g of lapatinib ditosylate are obtained, corresponding to an overall molar yield of 71%. HPLC purity A/A % 99.9%.

Example 8

Preparation of Lapatinib Ditosylate Monohydrate

Under an atmosphere of nitrogen, 50.0 g of Lapatinib ditosylate and 500 mL of water are loaded into a four-necked glass round-bottomed flask fitted with a mechanical stirrer, condenser and thermometer. This mixture is stirred for 36 hours at room temperature. The product is filtered, draining thoroughly, and then washed with the same mother liquor. The product is dried at room temperature inside a round-bottomed flask fitted with a stirrer under a stream of nitrogen.

The product is then dried for 24 hours at 55° C. until obtaining a K.F. value of around 1.92%. 51 g of product are obtained, giving a quantitative molar yield.

Example 9

Preparation of 2,2,2-trifluoro-N-{[5-(4-hydroxyquinazolin-6-yl) furan-2-yl]methyl}-N-[2-(methylsulfonyl)ethyl]acetamide of Formula (IV, R=CF$_3$(CO))—According to Step a-bis and b-bis, and a Preferred Embodiment of the Invention Synthetic scheme

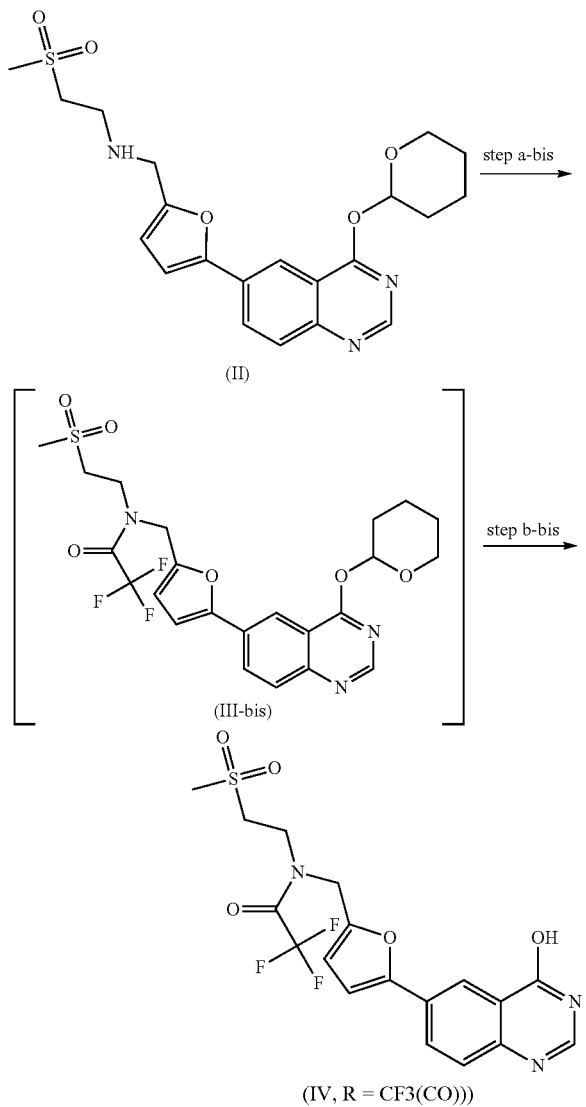

A glass round bottomed flask equipped with condenser, mechanical stirrer and thermometer, was charge under nitrogen atmosphere with 62.9 g (1 equiv) of compound of formula (II). Three azeotropic distillation were performed to residue with heptanes (3×315 mL, 3×5 V) to remove water until KF<1000 ppm. Then, 315 mL (5 V) of anhydrous dioxane were added and were cautiously charged with a dosing funnel, keeping the temperature at 20-25° C., (exothermic reaction, trifluoroacetic acid is formed) 68.9 g (46.3 mL, 1.5 equiv.) of trifluoroacetic anhydride. Once the dosage was completed the mixture was stirred at 90-95° C. for 3 hours. Checked the conversion via HPLC (samples taken every 30 min reveal rapid and complete conversion of intermediate of formula (II) into intermediate of formula (III-bis) which then converts to desired product of formula (IV, R=CF$_3$(CO))). When the reaction was complete, the mixture was cooled at 20-25° C. and, cautiously, 630 mL (10 V) of purified water were added. The mixture was then cooled down at 0-5° C. and stirred for 1-2 h. The slurry was filtered and the cake washed with 2×63 mL (2×1V) of pre-cooled purified water. The solid was dried in vacuo at 40-45° C. for at least 10 hours, until KF<0.5%. 57.7 g of product were obtained for a molar yield of 89.3%. HPLC purity A/A % 92-93%.

Example 10

Preparation of 2,2,2-trifluoro-N-[2-(methylsulfonyl)ethyl]-N-({5-[4-(tetrahydro-2H-pyran-2-yloxy)quinazolin-6-yl]furan-2-yl}methyl) acetamide of Formula (III—bis, R=CF$_3$(CO))

Synthetic scheme

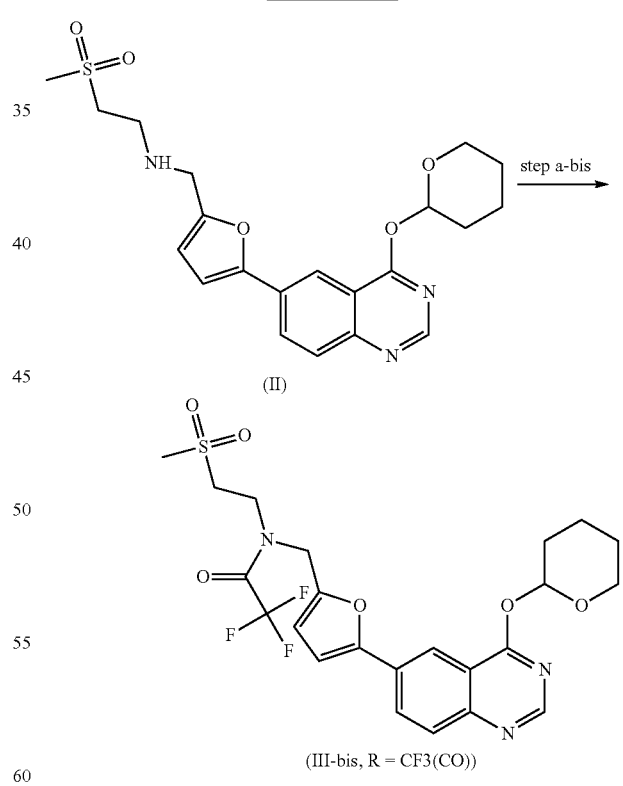

A glass round bottomed flask equipped with condenser, stirrer and thermometer, was charged under nitrogen atmosphere with 2.0 g (1 equiv.) of compound of formula (II). Three azeotropic distillation are performed to residue with heptanes (3×10 mL, 3×5 V) to remove water until KF<1000 ppm. Then 10 mL (5 V) of anhydrous DMF were charged followed by 1.59 g (1.62 mL, 2.5 equiv.) of triethylamine.

Keeping the T at 20-25 OC, with a dosing funnel (exothermic reaction) 1.46 g (0.98 mL, 1.5 equiv.) of trifluoroacetic anhydride were cautiously added. Once the dosage was completed the mixture was stirred at 50-55° C. for 1 hour. Checked the conversion via HPLC, when the reaction was complete, the mixture was cooled at 20-25° C. and cautiously 20 mL (10 V) of purified water were added. Then 20 mL (2 V) of dichloromethane were added. The mixture was stirred and layers were separated. The aqueous layer was extracted again with 2×20 mL (2×10V) of dichloromethane. The collected organic layers were joined are washed with 20 mL (10 V) of brine. The organic phase was dried on sodium sulfate and evaporate to residue. 2.25 g of product were obtained as an orange oil, for a molar yield of 92.0%.

Example 11

Preparation of 2,2,2-trifluoro-N-{[5-(4-hydroxyquinazolin-6-yl) furan-2-yl]methyl}-N-[2-(methylsulfonyl)ethyl]acetamide of Formula (IV, R=CF₃(CO))

Synthetic scheme

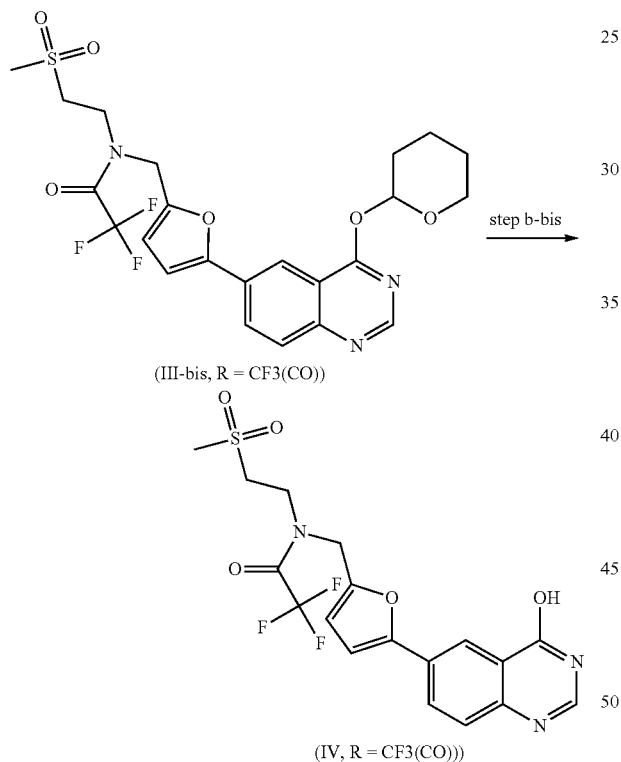

A glass round bottomed flask equipped with condenser, stirrer and thermometer, was charged under nitrogen atmosphere 8.9 g (1 equiv) di compound of formula (III-bis, R=CF₃(CO)). 80 mL (9 V) of acetonitrile were then added and the mixture was stirred at 40° C. A solution of 2.5 g (1.35 mL, 1.5 equiv.) of sulfuric acid in 9 mL (9 V) of acetonitrile was added over 15 min. The mixture was stirred at 40° C. for 5 hours and the conversion was checked via HPLC. The mixture was cooled at temperature of 20-25° C. and 100 mL (11 V) of purified water were added. The mixture was stirred for 1 hour at 20-25° C. and the slyrry was filtered and the cake was washed with con 2×9 mL (2×9 V) of purified water. The solid was dried in vacuo at 50° C. for at least 8 hours. 6.6 g of product were obtained for a molar yield of 88.2%. HPLC purity A/A % 96-97%.

The invention claimed is:
1. A process for preparing lapatinib of formula (I):

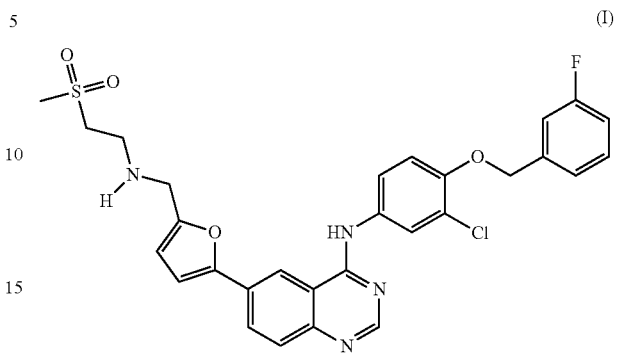

or a salt thereof, comprising:
(a) Protecting the compound 6-[5-({[2-(methylsulphonyl)ethyl]amino}methyl)furan-2-yl]quinazolin-4-ole of formula (III):

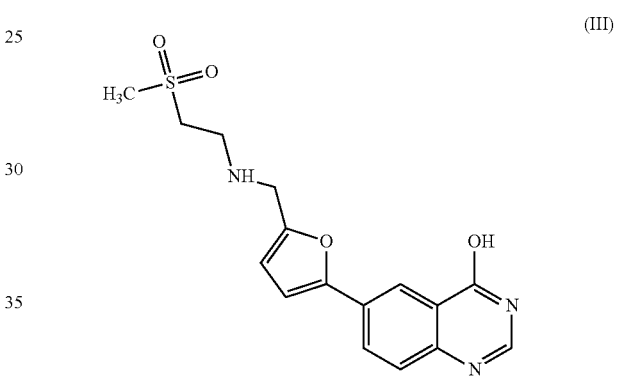

or a salt thereof,
to give the N-protected-6-[5-({[2-(methylsulphonyl)ethyl]amino}methyl)furan-2-yl]quinazolin-4-ole of formula (IV):

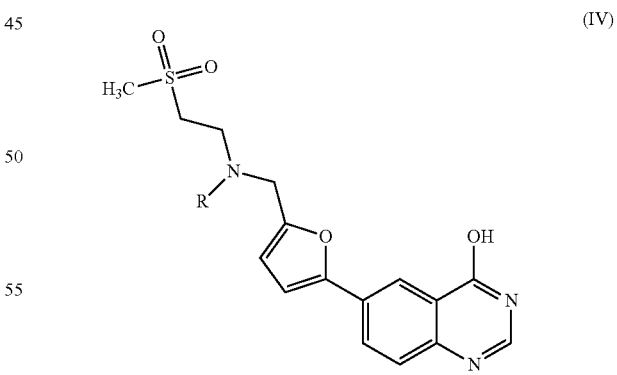

wherein R is chosen from methyl oxycarbonyl, ethyl oxycarbonyl, 9-(2-Sulfo)fluorenylmethyl oxycarbonyl, 9-(2,7-Dibromo)fluorenylmethyl oxycarbonyl, 17-Tetrabenzo[a,c,g,i]fluorenylmethyl oxycarbonyl (Tbfmoc), 2-Chloro-3-indenylmethyl oxycarbonyl (Climoc), Benz[f]inden-3-ylmethyl oxycarbonyl (Bimoc), 2-Phosphonioethyl oxycarbonyl (Peoc), 1-Methyl-1-(triphenylphosphonio)ethyl (2-Triphenylphosphonioisopropyl) oxycarbonyl (Ppoc), 1,1-Dimethyl-2-cyanoethyl oxycarbonyl, 2-Dansylethyl oxycarbonyl (Dnseoc), 2-(4-Nitrophenyl)ethyl oxycarbonyl (Npeoc), m-Chloro-p-acyloxybenzyl oxycarbonil, 9-Fluorenylmethyl oxycarbonyl (Fmoc), formyl (CO)H, acetyl $CH_3(CO)$, trifluoroacetyl $CF_3(CO)$, difluoroacetyl $CHF_2(CO)$, monofluoroacetyl $CH_2F(CO)$, trichloroacetyl $CCl_3(CO)$, dichloroacetyl $CHCl_2(CO)$, monochloroacetyl $CH_2Cl(CO)$, and 2-(Trimethylsilyl)ethanesulfonyl;

(b) Converting the intermediate of formula (IV) to give the N-protected-N-{[5-(4-substituted-quinazolin-6-yl)furan-2-yl]methyl}-2-(methylsulphonyl)ethanamine of formula (V):

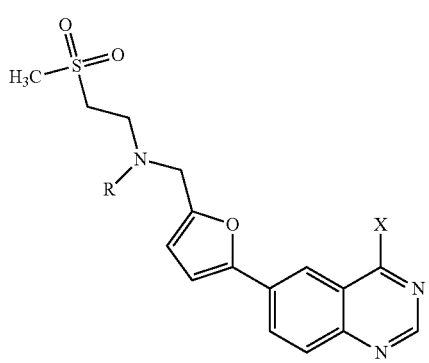

(V)

wherein X is chosen from fluorine, chlorine, bromine, iodine, O-Ms (mesylate), O-Ts (tosylate), O-Tf (triflate), ethanesulfonate (esylate), benzenesulfonate (besylate), p-bromobenzenesulfonate (brosylate), and p-nitrobenzenesulfonate (nosylate);

(c) Reacting the intermediate of formula (V) with 3-chloro-4-[(3-fluorobenzyl)oxy]aniline of formula (VI):

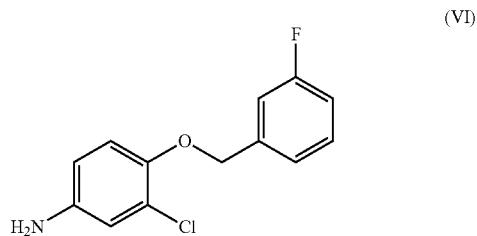 [SMILES: Nc1ccc(OCc2cccc(F)c2)c(Cl)c1]

(VI)

to give the N-protected lapatinib of formula (VII):

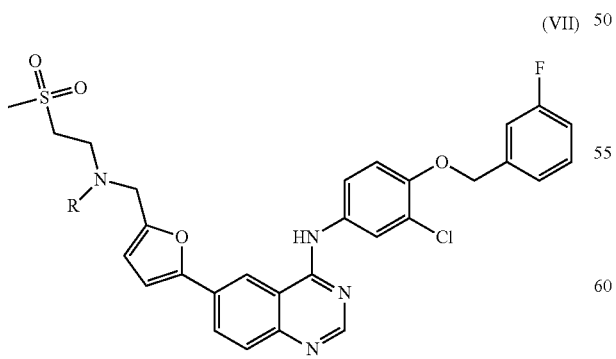

(VII)

and (d) Deprotecting N-protected lapatinib of formula (VII) to give lapatinib of formula (I), or a pharmaceutically acceptable salt thereof.

2. The process of claim 1, wherein R is chosen from acetyl $CH_3(CO)$, trifluoroacetyl $CF_3(CO)$, difluoroacetyl $CHF_2(CO)$, monofluoroacetyl $CH_2F(CO)$, trichloroacetyl $CCl_3(CO)$, dichloroacetyl $CHCl_2(CO)$, and monochloroacetyl $CH_2Cl(CO)$.

3. The process of claim 2, wherein R is trifluoroacetyl.

4. The process of claim 1, wherein X is chosen from fluorine, chlorine, bromine, iodine, O-Ms (mesylate), O-Ts (tosylate), O-Tf (triflate), and benzenesulfonate (besylate).

5. The process of claim 4, wherein X is chlorine.

6. The process of claim 1, wherein R is trifluoroacetyl and X is chlorine.

7. The process of claim 1, wherein the compound of formula (III) is in form of a sulfate salt.

8. The process of claim 1, wherein it is not necessary to isolate the intermediates of formulas (V) and (VII).

9. The process of claim 1, wherein the compound of formula (IV) is converted to lapatinib without isolating any intermediate.

10. The process of claim 1, wherein step b) is carried out by a reagent chosen from $POCl_3$, $SOCl_2$, $(COCl)_2$, and $PBr_3$.

11. The process of claim 10, wherein the reagent is $SOCl_2$.

12. The process of claim 1, wherein step b) is carried out by a reagent chosen from a sulphonyl halide and a sulphonic anhydride.

13. The process of claim 12, wherein the reagent is chosen from mesylchloride, tosylchloride, tosyl anhydride, and triflyc anhydride.

14. The process of claim 1, wherein step b) is carried out in an organic solvent.

15. The process of claim 14, wherein the solvent is chosen from toluene, acetonitrile, and dioxane.

16. The process of claim 15, wherein the solvent is dioxane.

17. The process of claim 1, wherein lapatinib salt is chosen from lapatinib ditosylate and lapatinib ditosylate monohydrate.

18. The process of claim 17, wherein lapatinib is lapatinib ditosylate monohydrate.

19. The process of claim 17, wherein lapatinib is lapatinib ditosylate.

20. A process for preparing lapatinib of formula (I):

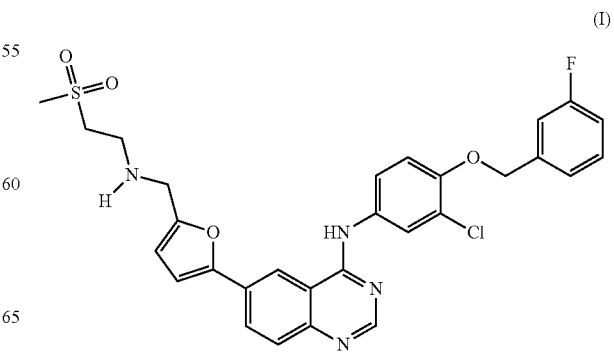

(I)

or a pharmaceutically acceptable salt thereof, comprising:

(a) Protecting the compound 6-[5-({[2-(methylsulphonyl)ethyl]amino}methyl)furan-2-yl]quinazolin-4-ole of formula (III):

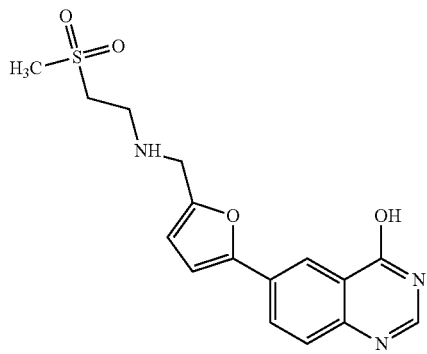

(III)

or a salt thereof, to give the N-protected-6-[5-({[2-(methylsulphonyl)ethyl]amino}methyl)furan-2-yl]quinazolin-4-ole of formula (IV):

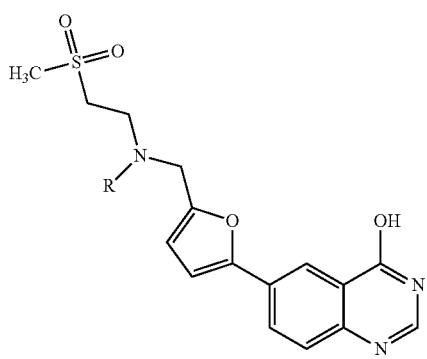

(IV)

wherein R is chosen from acetyl CH$_3$(CO), trifluoroacetyl CF$_3$(CO), difluoroacetyl CHF$_2$(CO), monofluoroacetyl CH$_2$F(CO), trichloracetyl CCl$_3$(CO), dichloroacetyl CHCl$_2$(CO), and monochloroacetyl CH$_2$Cl(CO);

(b) Converting the intermediate of formula (IV) to give the N-protected-N-{[5-(4-substituted-quinazolin-6-yl)furan-2-yl]methyl}-2-(methylsulphonyl)ethanamine of formula (V):

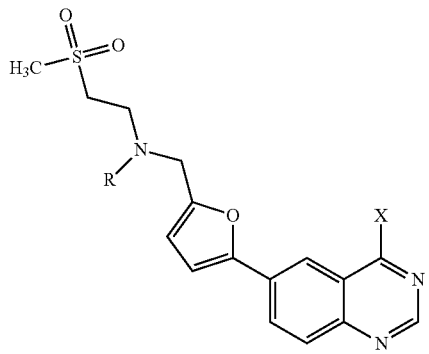

(V)

wherein X is chosen from fluorine, chlorine, bromine, iodine, O-Ms (mesylate), O-Ts (tosylate), O-Tf (triflate), and benzenesulfonate (besylate);

(c) Reacting the intermediate of formula (V) with 3-chloro-4-[(3-fluorobenzyl)oxy]aniline of formula (VI):

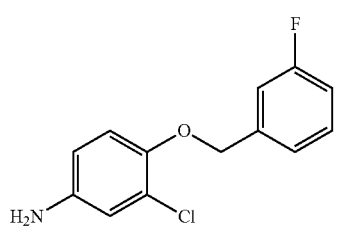

(VI)

to give the N-protected lapatinib of formula (VII):

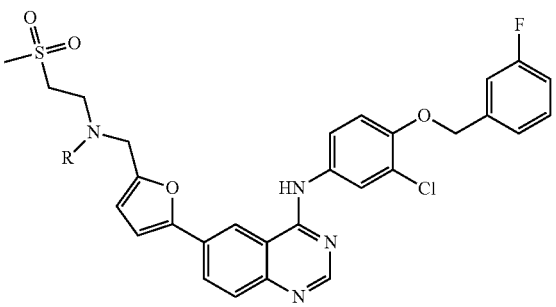

(VII)

and (d) Deprotecting N-protected lapatinib of formula (VII) to give lapatinib of formula (I), or a salt thereof.

21. The process of claim 20, wherein lapatinib is lapatinib ditosylate monohydrate.

22. The process of claim 20, wherein lapatinib is lapatinib ditosylate.

* * * * *